(12) United States Patent
Cui et al.

(10) Patent No.: US 11,529,314 B2
(45) Date of Patent: Dec. 20, 2022

(54) LIPID-BASED NANOPARTICLES FOR ENCAPSULATION AND SUSTAINED RELEASE OF THERAPEUTIC AGENTS

(71) Applicant: BOARD OF REGENTS, THE UNIVERSITY OF TEXAS SYSTEM, Austin, TX (US)

(72) Inventors: Zhengrong Cui, Austin, TX (US); Abdulaziz Aldayel, Austin, TX (US); Hannah O'Mary, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 16/762,654

(22) PCT Filed: Nov. 7, 2018

(86) PCT No.: PCT/US2018/059534
§ 371 (c)(1),
(2) Date: May 8, 2020

(87) PCT Pub. No.: WO2019/094405
PCT Pub. Date: May 16, 2019

(65) Prior Publication Data
US 2020/0268678 A1 Aug. 27, 2020

Related U.S. Application Data

(60) Provisional application No. 62/584,450, filed on Nov. 10, 2017.

(51) Int. Cl.
| | |
|---|---|
| A61K 9/51 | (2006.01) |
| A61K 47/54 | (2017.01) |
| A61K 47/69 | (2017.01) |
| A61K 47/60 | (2017.01) |
| A61K 9/127 | (2006.01) |
| A61K 31/395 | (2006.01) |
| A61K 31/573 | (2006.01) |
| A61K 31/713 | (2006.01) |
| A61K 47/28 | (2006.01) |
| B82Y 5/00 | (2011.01) |

(52) U.S. Cl.
CPC .......... *A61K 9/5123* (2013.01); *A61K 9/1272* (2013.01); *A61K 9/5192* (2013.01); *A61K 31/395* (2013.01); *A61K 31/573* (2013.01); *A61K 31/713* (2013.01); *A61K 47/28* (2013.01); *A61K 47/543* (2017.08); *A61K 47/60* (2017.08); *A61K 47/6929* (2017.08); *B82Y 5/00* (2013.01)

(58) Field of Classification Search
None
See application file for complete search history.

(56) References Cited

U.S. PATENT DOCUMENTS

| | | | |
|---|---|---|---|
| 2008/0213350 A1* | 9/2008 | Ko | C12N 15/88 424/450 |
| 2008/0311040 A1* | 12/2008 | Berry | A61P 43/00 514/1.1 |
| 2009/0312402 A1 | 12/2009 | Contag et al. | |
| 2013/0243848 A1 | 9/2013 | Lobovkina et al. | |

OTHER PUBLICATIONS

International Search Report and Written Opinion in PCT/US2018/059534. dated Apr. 15, 2019. 11 pages.
Aldayel, et al., "Acid-Sensitive Sheddable PEGylated PLGA Nanoparticles Increase the Delivery of TNF-Alpha siRNA in Chronic Inflammation Sites" Mol Ther Nucleic Acids. Jul. 2016. vol. 5, No. 7, p. e340. pp. 1-10.
Internal nanotechnology task force for USFDA. 2006, Nanomedicine-Uk, 1, 264-264.
Aldayel, A.M., Naguib, Y.W., O/'Mary, H.L., Li, X., Niu, M., Ruwona, T.B. and Cui, Z. (2016) Acid-Sensitive Sheddable PEGylated PLGA Nanoparticles Increase the Delivery of TNF-[alpha] siRNA in Chronic Inflammation Sites. Mol Ther Nucleic Acids, 5, e340.
Bendele, A.M., Chlipala, E.S., Scherrer, J., Frazier, J., Sennello, G., Rich, W.J. and Edwards, C.K., 3rd. (2000) Combination benefit of treatment with the cytokine inhibitors interleukin-1 receptor antagonist and PEGylated soluble tumor necrosis factor receptor type I in animal models of rheumatoid arthritis. Arthritis Rheum, 43, 2648-2659.
Chia, W.T., Chen, Y.W., Cheng, L.Y., Lee, H.S., Chang, D.M. and Sytwu, H.K. K2008) MMP-9 mRNA as a therapeutic marker in acute and chronic stages of arthritis induced by type II collagen antibody. J Formos Med Assoc, 107, 245-252.

(Continued)

*Primary Examiner* — Robert A Wax
*Assistant Examiner* — Quanglong N Truong
(74) *Attorney, Agent, or Firm* — Meunier Carlin & Curfman LLC

(57) ABSTRACT

Disclosed herein are nanoparticles comprising a lipid core comprising a sterol; and a complex comprising a cationic agent and a therapeutic agent, wherein the complex is encapsulated within the lipid core. Methods to produce the nanoparticle comprise: combining a cationic agent, a therapeutic agent, and a first water-immiscible solvent with a first aqueous solution, thereby forming a mixture comprising a complex comprising the cationic agent and the therapeutic agent; combining the mixture with a second waterim-miscible solvent, thereby forming an aqueous phase and an organic phase, and separating the organic phase comprising the complex; combining the organic phase comprising the complex with a sterol and a first water-miscible organic solvent; and dispersing the complex in a second aqueous solution to form a herein disclosed nanoparticle. Methods for treating a disease and for reducing nanoparticle burst rate are also disclosed.

22 Claims, 12 Drawing Sheets

(56) References Cited

OTHER PUBLICATIONS

Choi, B., Cui, Z.K., Kim, S., Fan, J., Wu, B.M. and Lee, M. (2015) Glutamine-chitosan modified calcium phosphate nanoparticles for efficient siRNA delivery and osteogenic differentiation. J Mater Chem B Mater Biol Med, 3, 6448-6455.

Choy, E.H. and Panayi, G.S. (2001) Cytokine pathways and joint inflammation in Yheumatoid arthritis. N Engl J Med, 344, 907-916.

Cun, D.M., Jensen, D.K., Maltesen, M.J., Bunker, M., Whiteside, P., Scurr, D., Foged, C. and Nielsen, H.M. (2011) High loading efficiency and sustained release of siRNA encapsulated in PLGA nanoparticles: Quality by design optimization and characterization. European Journal of Pharmaceutics and Biopharmaceutics, 77, 26-35.

D'Haens, G.R. (1999) Infliximab (Remicade), a new biological treatment for Crohn's disease. Ital J Gastroenterol Hepatol, 31, 519-520. Abstract.

Gao, S., Dagnaes-Hansen, F., Nielsen, E.J.B., Wengel, J., Besenbacher, F., Howard, K.A. and Kjems, J. (2009) The Effect of Chemical Modification and Nanoparticle Formulation on Stability and Biodistribution of siRNA in Mice. Mol Ther, 17, 1225-1233.

Howard, K.A., Paludan, S.R., Behlke, M.A., Besenbacher, F., Deleuran, B. and Kjems, J. (2009) Chitosan/siRNA nanoparticle-mediated TNF-alpha knockdown in peritoneal macrophages for anti-inflammatory treatment in a murine arthritis model. Mol Ther, 17, 162-168.

Jackson, A.L. and Linsley, P.S. (2010) Recognizing and avoiding siRNA off-target effects for target identification and therapeutic application. Nat Rev Drug Discov, 9, 57-67.

Jahoor, A., Patel, R., Bryan, A., Do, C., Krier, J., Watters, C., Wahli, W., Li, G., Williams, S.C. and Rumbaugh, K.P. (2008) Peroxisome proliferator-activated receptors mediate host cell proinflammatory responses to Pseudomonas aeruginosa autoinducer. J Bacteriol, 190, 4408-4415.

Kanasty, R.L., Whitehead, K.A., Vegas, A.J. and Anderson, D.G. (2012) Action and Yeaction: the biological response to siRNA and its delivery vehicles. Mol Ther, 20, 513-524.

Khachigian, L.M. (2006) Collagen antibody-induced arthritis. Nat Protoc, 1, 2512-2516.

Kim, S.S., Ye, C., Kumar, P., Chiu, I., Subramanya, S., Wu, H., Shankar, P. and Manjunath, N. (2010) Targeted delivery of siRNA to macrophages for anti-inflammatory treatment. Mol Ther, 18, 993-1001.

Komano, Y., Yagi, N., Onoue, I., Kaneko, K., Miyasaka, N. and Nanki, T. (2012) Arthritic joint-targeting small interfering RNA-encapsulated liposome: implication for treatment strategy for rheumatoid arthritis. J Pharmacol Exp Ther, 340, 109-113.

Lee, S.J., Lee, A., Hwang, S.R., Park, U.S., Jang, J., Huh, M.S., Jo, D.G., Yoon, S.Y., Byun, Y., Kim, S.H et al. (2014) TNF-alpha gene silencing using polymerized siRNA/thiolated glycol chitosan nanoparticles for rheumatoid arthritis. Mol Ther, 22, 397-408.

Leng, Q., Woodie, M.C., Lu, P.Y. and Mixson, A.J. (2009) Advances in Systemic siRNA Delivery. Drug Future, 34, 721-737.

Lobovkina, T., Jacobson, G.B., Gonzalez-Gonzalez, E., Hickerson, R.P., Leake, D., Kaspar, R.L., Contag, C.H. and Zare, R.N. (2011) In vivo sustained release of siRNA from solid lipid nanoparticles. ACS Nano, 5, 9977-9983.

Lu, L.D., Stump, K.L. and Seavey, M.M. (2010) Novel method of monitoring trace cytokines and activated STAT molecules in the paws of arthritic mice using multiplex bead technology. BMC Immunol, 11, 55.

Presumey, J., Salzano, G., Courties, G., Shires, M., Ponchel, F., Jorgensen, C., Apparailly, F. and De Rosa, G. (2012) PLGA microspheres encapsulating siRNA anti-TNFalpha: efficient RNAi-mediated treatment of arthritic joints. Eur J Pharm Biopharm, 82, 457-464.

Schiff, M.H., Burmester, G.R., Kent, J.D., Pangan, A.L., Kupper, H., Fitzpatrick, S.B. and Donovan, C. (2006) Safety analyses of adalimumab (HUMIRA) in global clinical trials and US postmarketing surveillance of patients with rheumatoid arthritis. Ann Rheum Dis, 65, 889-894.

Schreiber, S. (2011) Certolizumab pegol for the treatment of Crohn's disease. Therap Adv Gastroenterol, 4, 375-389.

Te Boekhorst, B.C., Jensen, L.B., Colombo, S., Varkouhi, A.K., Schiffelers, R.M., Lammers, T., Storm, G., Nielsen, H.M., Strijkers, G.J., Foged, C et al. (2012) MRI-assessed therapeutic effects of locally administered PLGA nanoparticles loaded with anti-inflammatory siRNA in a murine arthritis model. J Control Release, 161, 772-780.

Tseng, J.C. and Kung, A.L. (2013) In vivo imaging method to distinguish acute and chronic inflammation. J Vis Exp, 78, 50690.

Van de Putte, L.B., Rau, R., Breedveld, F.C., Kalden, J.R., Malaise, M.G., van Riel, P.L., Schattenkirchner, M., Emery, P., Burmester, G.R., Zeidler, H et al. (2003) Efficacy and safety of the fully human anti-tumour necrosis factor alpha monoclonal antibody adalimumab (D2E7) in DMARD refractory patients with rheumatoid arthritis: a 12 week, phase II study. Ann Rheum Dis, 62, 1168-1177.

Wang, J., Lu, Z., Wientjes, M.G. and Au, J.L. (2010) Delivery of siRNA therapeutics: barriers and carriers. AAPS J, 12, 492-503.

Weinblatt, M.E., Bingham, C.O., 3rd, Mendelsohn, A.M., Kim, L., Mack, M., Lu, J., Baker, D. and Westhovens, R. (2013) Intravenous golimumab is effective in patients with active rheumatoid arthritis despite methotrexate therapy with responses as early as week 2: results of the phase 3, randomised, multicentre, double-blind, placebo-controlled GO-FURTHER trial. Ann Rheum Dis, 72, 381-389.

Ye, C., Bhan, A.K., Deshpande, V., Shankar, P. and Manjunath, N. (2013) Silencing TNF-alpha in macrophages and dendritic cells for arthritis treatment. Scand J Rheumatol, 42, 266-269.

Zhou, Z., Li, H., Wang, K., Guo, Q., Li, C., Jiang, H., Hu, Y., Oupicky, D. and Sun, M. (2017) Bioreducible Cross-Linked Hyaluronic Acid/Calcium Phosphate Hybrid Nanoparticles for Specific Delivery of siRNA in Melanoma Tumor Therapy. ACS Appl Mater Interfaces, 9, 14576-14589.

Zhu, S.J., Wonganan, P., Lansakara-P, D.S.P., O'Mary, H.L., Li, Y. and Cui, Z.R. (2013) The effect of the acid-sensitivity of 4-(N)-stearoyl gemcitabine-loaded micelles on drug resistance caused by RRM1 overexpression. Biomaterials, 34, 2327-2339.

International Preliminary Report on Patentability issued for Application No. PCT/US2018/059534, dated May 22, 2020.

* cited by examiner

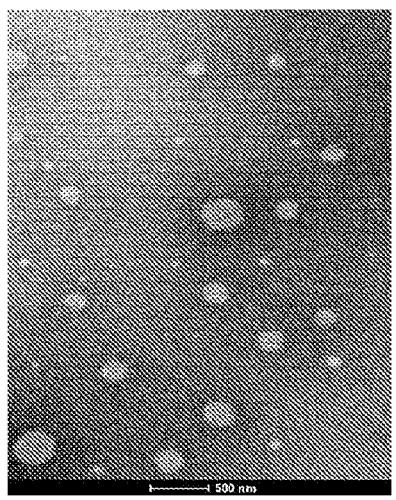
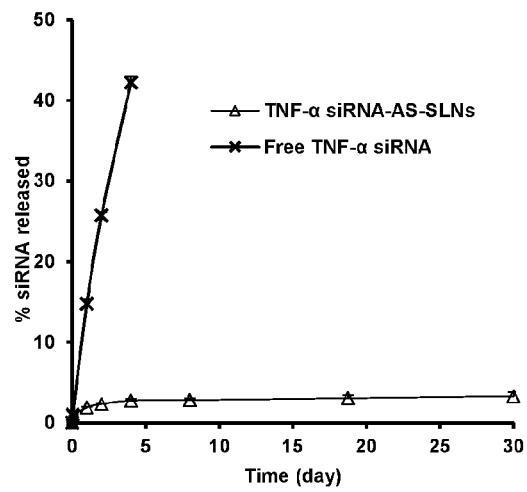
FIG. 2A
FIG. 2B

LIPID-BASED NANOPARTICLES FOR ENCAPSULATION AND SUSTAINED RELEASE OF THERAPEUTIC AGENTS

CROSS-REFERENCE TO RELATED APPLICATIONS

This application claims priority to and is a United States National Phase Patent Application of International Patent Application No. PCT/US2018/059534, filed on Nov. 7, 2018, which claims benefit of U.S. Provisional Application No. 62/584,450, filed Nov. 10, 2017, both of which are incorporated by reference herein.

STATEMENT REGARDING FEDERALLY SPONSORED RESEARCH

This invention was made with government support under Grant No. CA135274 awarded by the National Institutes of Health. The Government has certain rights in the invention.

FIELD

The disclosure generally relates to nanoparticles, more specifically lipid-based nanoparticles, capable of encapsulating hydrophilic compounds in a lipid core. The disclosure further relates to methods to make nanoparticles and methods to treat a disease by administering nanoparticle compositions.

BACKGROUND

Inflammation is an acute, signal-mediated process in response to harmful stimuli. It involves the infiltration of immune cells and soluble mediators such as tumor necrosis factor alpha (TNF-α) to the site of inflammation. Chronic inflammation-related diseases such as rheumatoid arthritis (RA) may develop in response to failure to resolve the acute inflammation.

Anti-TNF-α therapies have proven effective in treating arthritis. In the past decade, there has been a growing interest in using TNF-α small interfering RNA (siRNA) to selectively reduce the production of the proinflammatory TNF-α cytokine to treat arthritis. Small interfering RNA has been formulated into nanoparticles to address issues related to siRNA's short half-life, poor extravasation from blood vessels to target tissues, poor cellular uptake, and potential immunogenicity. Data from several studies showed that TNF-α siRNA loaded nanoparticles or nanocomplexes, prepared with polymers (e.g., chitosan, poly (lactic-co-glycolic) acid (PLGA)) or lipids, can be used to treat arthritis in mouse models. Various methods and compositions have been used to formulate nanoparticles with high siRNA encapsulation efficiency. However, high burst release of siRNA (20% or more within two days) is a typical problem for most siRNA formulations that have a high encapsulation efficiency. Therefore, there continues to be a need for particle formulations that have high siRNA encapsulation efficiency and low siRNA burst release. The compositions and methods disclosed herein address these and other needs.

SUMMARY

The disclosed subject matter relates to lipid based nanoparticles and methods for the manufacture and use thereof. The present disclosure addresses at least a portion of the problems described above by providing a nanoparticle capable of highly efficient therapeutic agent encapsulation and a slow burst release of encapsulated therapeutic agent. The nanoparticle compositions facilitate delivery of a therapeutic agent to desired sites in a subject's body in part by forming and maintaining stable encapsulation of the therapeutic agent. The nanoparticles therefore avoid unintended loss or undesirable systemic delivery of encapsulated therapeutic agent. The disclosure further provides novel methods of making and using the inventive nanoparticles, which can be adapted to provide an array of nanoparticle compositions and uses thereof. The compositions and methods disclosed herein address these and other needs.

In one aspect, disclosed herein is a nanoparticle composition comprising: a lipid core comprising a sterol; and a complex comprising a cationic agent and a therapeutic agent, wherein the complex is encapsulated within the lipid core. In some embodiments, the therapeutic agent is siRNA. In some embodiments, the lipid core further comprises a glucocorticoid. In some embodiments, the nanoparticle further comprises an acid-sheddable PEG.

In another aspect, provided herein are methods for preparing lipid-based nanoparticle compositions comprising: a) combining a cationic agent, a therapeutic agent, and a first water-immiscible solvent with a first aqueous solution, thereby forming a mixture comprising a complex comprising the cationic agent and the therapeutic agent; b) combining the mixture with a second water-immiscible solvent, thereby forming an aqueous phase and an organic phase, and separating the organic phase comprising the complex; c) combining the organic phase comprising the complex with a sterol and a first water-miscible organic solvent; and d) dispersing the complex in a second aqueous solution to form a nanoparticle comprising a lipid core comprising a sterol; and a complex comprising a cationic agent and a therapeutic agent, wherein the complex is encapsulated within the lipid core. In some embodiments, prior to step b), the mixture is combined with a second water-miscible organic solvent. In some embodiments, the method further comprises removing at least a portion of the second water-immiscible solvent in the organic phase of step c) after combining the organic phase comprising the complex with the sterol but before combining the water-miscible organic solvent.

In another aspect, provided herein are methods for treating a subject with a disease, comprising: administering to the subject a nanoparticle comprising a lipid core comprising a sterol; and a complex comprising a cationic agent and a therapeutic agent, wherein the complex is encapsulated within the lipid core.

In another aspect, provided herein are methods of reducing the burst rate of a therapeutic agent from a nanoparticle comprising encapsulating the therapeutic agent in a nanoparticle comprising a lipid core comprising a sterol; and a complex comprising a cationic agent and a therapeutic agent, wherein the complex is encapsulated within the lipid core, wherein the burst rate of the therapeutic agent from the nanoparticle is 50 percent or less within 30 days.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

In FIG. 1A a preparation of siRNA-DOTAP complexes in water-chloroform-methanol monophase. In FIG. 1B a preparation of siRNA-incorporated solid lipid nanoparticles is formed.

FIGS. 2A and 2B show the physical characterization of the AS-TNF-α siRNA-SLNs. FIG. 2A is a representative TEM image of AS-TNF-α siRNA-SLNs. In FIG. 2B, the in vitro release profile of fluorescently-labeled siRNA from AS-siRNA-SLNs. The diffusion of the siRNA across the dialysis membrane is also included to show that the diffusion of siRNA across the membrane is not the rate-limiting step. Data are mean±S.E. (n=3).

In FIG. 3A, in vitro confirmation of the acid-sensitivity of the PEGylation of the AS-siRNA-SLNs. J774A.1 cells ($2.5 \times 10^5$) were seeded in 24-well plates. Twenty hours later, the medium was replaced with serum-free DMEM containing fluorescein-labeled AS-siRNA-SLNs or AI-siRNA-SLNs that were pre-incubated at pH 6.8 or pH 7.4 for 6 h. The cells were washed after 50 min of incubation and lysed, and the fluorescence intensity was measured and normalized to protein concentration (a-c, p<0.05). FIG. 3B shows the, evaluation of the function of the TNF-α siRNA in down-regulating TNF-α release. J774A.1 cells ($1 \times 10^4$) were seeded in 96-well plates. Twenty hours later, the medium was replaced with serum-free DMEM containing AS-TNF-α siRNA-SLNs (siRNA=50 ng/well). Controls include AS-siRNA-SLNs containing control siRNA, TNF-α siRNA complexes with GeneSilencer, or sterile PBS. After 4 h of incubation, the medium was replaced with fresh medium. LPS (100 ng/ml) was added 19 h later, and the cells were incubated for five additional hours. TNF-α level in culture media was measured and normalized to cell numbers estimated with an MTT assay (* p<0.05).

FIG. 4A shows in vivo fluorescence images of inflamed mouse feet at 24 h after i.v. injection of PBS, AI-siRNA-SLNs or AS-siRNA-SLNs. The nanoparticles were labeled with TopFluor cholesterol. FIG. 4B shows mean fluorescence intensity values of inflamed mouse feet 6 or 24 h after mice were i.v. injected with AI-siRNA-SLNs or AS-siRNA-SLNs. FIG. 4C shows normalized fluorescence intensity values in major organs and inflamed foot of mice 24 h after they were i.v. injected with AI-siRNA-SLNs or AS-siRNA-SLNs. In FIGS. 4B and 4C, data are mean±S.E. (n=3-5).

FIG. 5A shows representative photographic images of healthy feet or inflamed feet in DBA/1 mice with CIA taken 31 days post-injection. FIG. 5B shows representative micro-CT images of healthy feet or inflamed feet in DBA/1 mice with CIA taken 31 days post-injection. FIG. 5C shows IVIS™ images of the left hind legs of CIA mice 48 h after mice were i.v. injected with fluorescently-labeled siRNA, free or in AS-siRNA-SLNs. FIG. 5D shows mean normalized fluorescence intensity values in all inflamed hind legs 48 h after mice were i.v. injected with free siRNA or AS-siRNA-LCDs. Data are mean S.D. (n=3-4, both rear legs).

FIG. 6A shows the effect of AS-TNF-a siRNA-SLNs on hind leg paw thickness (* p<0.05, AS-TNF-a siRNA-SLNs vs. AS-Cont siRNA-SLNs on days 6 and 8). FIG. 6B shows representative 3D X-ray micro-CT reconstructed images of calcaneus bone. FIG. 6C shows relative bone density loss measured by ImageJ. FIGS. 6D and 6E show H&E (FIG. 6D) and Safranin-O images (FIG. 6E) of arthritic joints. FIGS. 6F and 6G show the average scores of the severity of pathological factors such as synovial hypertrophy, density of resident cells and inflammatory cell infiltrates, matrix degradation and osteolysis after H&E staining (FIG. 6F) or safranin-O staining (FIG. 6G). Data are mean±S.E. (n=3-5). (* p≤0.05).

FIG. 10A is a representative TEM image of AS-MTX-siRNA-DOTAP-SLNs. FIG. 10B is a representative TEM image of AS-MTX-siRNA-DOTAP-SLNs at higher magnification.

DETAILED DESCRIPTION

Figure 1A:
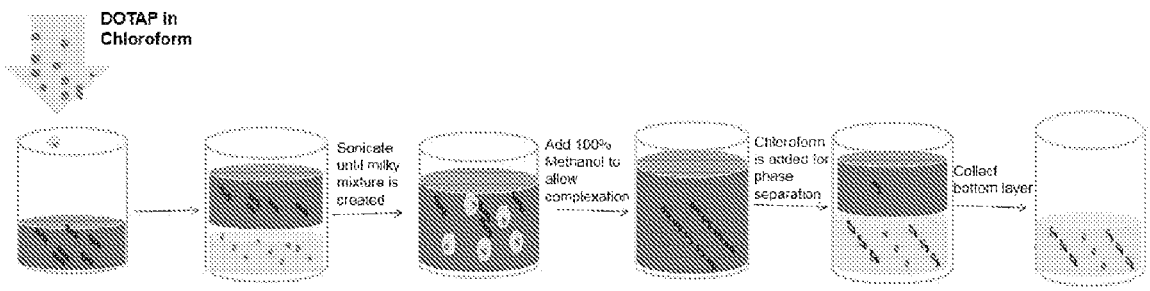
FIGS. 1A and 1B are schematics depicting the preparation of AS-TNF-α siRNA-SLNs.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular nanoparticle is disclosed and discussed and a number of modifications that can be made to the nanoparticle are discussed, specifically contemplated is each and every combination and permutation of the nanoparticle and the modifications that are possible unless specifically indicated to the contrary. Thus, if a class of nanoparticles A, B, and C are disclosed as well as a class of nanoparticles D, E, and F and an example of a combination nanoparticle, or, for example, a combination nanoparticle comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

"Administration" to a subject includes any route of introducing or delivering to a subject an agent. Administration can be carried out by any suitable route, including oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time or essentially immediately following one another. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., rheumatoid arthritis). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of chronic inflammation. Therapeutically effective amounts of a given therapeutic agent will typically vary with respect to factors such as the type and severity of the disorder or disease being treated and the age, gender, weight, and general condition of the subject. Thus, it is not always possible to specify a quantified "therapeutically effective amount." However, an appropriate "therapeutically effective amount" in any subject case may be determined by one of ordinary skill in the art using routine experimentation. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. It is understood that, unless specifically stated otherwise, a "therapeutically effective amount" of a therapeutic agent can also refer to an amount that is a prophylactically effective amount. In some instances, a desired biological or medical response is achieved following administration of multiple dosages of the composition to the subject over a period of days, weeks, or years.

"Treat," "treating," "treatment," and grammatical variations thereof as used herein, include the administration of a composition with the intent or purpose of partially or completely, delaying, curing, healing, alleviating, relieving, altering, remedying, ameliorating, improving, stabilizing, mitigating, and/or reducing the intensity or frequency of one or more a diseases or conditions, a symptom of a disease or condition, or an underlying cause of a disease or condition. Treatments according to the invention may be applied, prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for day(s) to years prior to the manifestation of symptoms of an infection.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value" 10" is disclosed, then "about 10" is also disclosed.

Lipid-Based Nanoparticle Compositions

It is understood that the nanoparticles of the present disclosure can be used in combination with the various compositions, methods, products, and applications disclosed herein.

Characteristics of ideal nanoparticles for delivery of therapeutic agents such as nucleic acids include a high encapsulation efficiency, high stability, and low burst release (of therapeutic agent). These properties ultimately result in high pharmacological efficacy and low toxicity in vivo.

The disclosure herein addresses needs in the art by providing for lipid-based nanoparticles which have high encapsulation efficiencies of therapeutic agents, for example anti-TNF-α siRNA, and low burst release. The nanoparticles may be formed by a lower toxicity method involving complexing a therapeutic agent with a biocompatible cationic agent, then incorporating the nanocomplexes into solid lipid nanoparticles prepared using a non-toxic sterol and, optionally, an additional lipid such as an anionic or neutral lipid (e.g., lecithin and/or cholesterol). Further, the nanoparticle can be responsive to particular stimuli by, for instance, addition of an acid-sensitive outer layer or coating (e.g., stearic acid-polyethylene glycol (2000) hydrazone conjugate). Nanoparticles PEGylated with the acid-sensitive stearoyl-PEG2000 have increased distribution and retention in chronic inflammation sites in a mouse model, by taking advantage of the relatively lower pH microenvironment in chronic inflammation sites. The nanoparticles have improved biodistribution in mouse models of chronic inflammation, and the nanoparticles had good efficacy in a mouse model with collagen antibody-induced arthritis (CAIA) that develops clinical features closely representative of RA in human, including increased capillary permeability, accumulation of white blood cells, and severe joint damage and bone erosion.

Disclosed herein are nanoparticle compositions, particularly lipid-based nanoparticle compositions. The nanoparticle contains a lipid core and a complex. The lipid core contains a sterol. The complex contains at least a cationic agent and a therapeutic agent. Further, the complex is encapsulated within the lipid core.

The nanoparticle contains a complex comprising a cationic agent and a therapeutic agent. The complex can contain one or more cationic agents. For example, the complex can contain a first cationic agent and a second cationic agent, wherein the first and the second cationic agents are the same agents. While use of a single specific cationic agent can produce more complexes having greater homogeneity, the number of cationic agents used is not particularly limited. Thus, in some embodiments, the complex can contain mixtures of numerous cationic agents. The complex can contain at least two, at least three, at least four, at least five, or more cationic agents. For example, the complex can contain a first cationic agent and a second cationic agent, wherein the first and the second cationic agents are different agents.

The complex can contain one or more therapeutic agents. For example, the complex can contain a first therapeutic agent and a second therapeutic agent, wherein the first and the second therapeutic agents are the same agents. While use of a single specific therapeutic agent can produce more complexes having greater homogeneity, the number of therapeutic agents used is not particularly limited. Thus, in some embodiments, the complex can contain mixtures of numerous therapeutic agents. The complex can contain at least two, at least three, at least four, at least five, or more therapeutic agents. For example, the complex can contain a first therapeutic agent and a second therapeutic agent, wherein the first and the second therapeutic agents are different agents. In some embodiments, the complex comprises a first therapeutic agent and a second therapeutic agent, wherein the first therapeutic agent comprises a polynucleotide (e.g., siRNA) and the second therapeutic agent comprises a small molecule (e.g., doxorubicin).

By "complex" it is meant that the cationic agent and the therapeutic agent are associated by any one or more intermolecular forces, for example by ionic, ion-dipole, dipole, London dispersion, van der Wall's, and/or hydrogen bonding forces. Further, a complex between the cationic agent and the therapeutic agent can be formed by hydrophobic interaction. The complex between the cationic agent and the therapeutic agent is reversible, so as to facilitate release of the therapeutic agent. To the extent covalent associations are readily reversible to facilitate release of the therapeutic agent, such associations between the cationic agent and the therapeutic agent are also envisioned. Complexation with the cationic agent facilitates, among other things, the encapsulation of the therapeutic agent within the lipid core.

The cationic agent can be any molecule having a net positive polarity or charge at or near physiological pH and capable of forming a complex with a therapeutic agent. In some embodiments, the cationic agent comprises a cationic lipid. In some embodiments, the cationic agent comprises an aromatic amine. In some embodiments, the cationic agent comprises a combination of a cationic lipid and an aromatic amine.

The cationic agent can comprise a cationic lipid. The cationic lipid can vary in head group composition, acyl chain composition and length, degree of polarity or charge, attachment or substitution of functional groups, degree of saturation or branching of acyl chain hydrocarbons, and other features. The net positive polarity or charge of the cationic lipid is primarily responsible for an overall net positive polarity or charge of the complex comprising the cationic lipid and a therapeutic agent.

Suitable cationic lipids include, but are not limited to, 1,2-dioleoyl-3-trimethylammonium-propane (DOTAP); N,N-dioleyl-N,N-dimethylammonium chloride ("DODAC"); N-(2,3-dioleyloxy)propyl)-N,N,N-trimethylammonium chloride ("DOTMA"); N,N-distearyl-N,N-dimethylammonium bromide ("DDAB"); N-(2,3-dioleyloxy)propyl)-N,N,N-trimethylammonium chloride ("DOTAP-Cl"); N-(1,2-dimyristyloxyprop-3-yl)-N,N-dimethyl-N-hydroxyethylammonium bromide ("DMRIE"), 3β-(N-(N',N'-dimethylaminoethane)carbamoyl)cholesterol ("DC-Chol"), dioctadecylamidoglycyl carboxyspermidine ("DOGS"); N-(1-(2,3-dioleyloxy)propyl)-N-(2-(sperminecarboxamido)ethyl)-N,N-dimethylammonium trifluoroacetate ("DOSPA"); 1-(2-(oleoyloxy)ethyl)-2-oleyl-3-(2-hydroxyethyl)imidazolinium; 1,2-dilinoleyloxy-N,N-dimethylaminopropane (DLinDMA); 1,2-dilinolenyloxy-N,N-dimethylaminopropane (DLenDMA); 2,2-dilinoleyl-4-(2-dimethylaminoethyl)-[1,3]-dioxolane (DLin-K-C2-DMA; "XTC2"); 2,2-dilinoleyl-4-(3-dimethylaminopropyl)-[1,3]-dioxolane (DLin-K-C3-DMA); 2,2-dilinoleyl-4-(4-dimethylaminobutyl)-[1,3]-dioxolane (DLin-K-C4-DMA); 2,2-dilinoleyl-5-dimethylaminomethyl-[1,3]-dioxane (DLin-K6-DMA); 2,2-dilinoleyl-4-N-methylpepiazino-[1,3]-dioxolane (DLin-K-MPZ); 2,2-dilinoleyl-4-dimethylaminomethyl-[1,3]-dioxolane (DLin-K-DMA); 1,2-dilinoleylcarbamoyloxy-3-dimethylaminopropane (DLin-C-DAP); 1,2-dilinoleyoxy-3-(dimethylamino)acetoxypropane (DLin-DAC); 1,2-dilinoleyoxy-3-morpholinopropane (DLin-MA); 1,2-dilinoleoyl-3-dimethylaminopropane (DLinDAP); 1,2-dilinoleylthio-3-dimethylaminopropane (DLin-S-DMA); 1-linoleoyl-2-linoleyloxy-3-dimethylaminopropane (DLin-2-DMAP); 1,2-dilinoleyloxy-3-trimethylaminopropane chloride salt (DLin-TMA.Cl); 1,2-dilinoleoyl-3-trimethylaminopropane chloride salt (DLin-TAP.Cl); 1,2-dilinoleyloxy-3-(N-methylpiperazino)propane (DLin-MPZ); 3-(N,N-dilinoleylamino)-1,2-propanediol (DLinAP); 3-(N,N-dioleylamino)-1,2-propanedio (DOAP); 1,2-dilinoleyloxo-3-(2-N,N-dimethylamino)ethoxypropane (DLin-EG-DMA); N,N-dioleyl-N,N-dimethylammonium chloride (DODAC); 1,2-dioleyloxy-N,N-dimethylaminopropane (DODMA); 1,2-distearyloxy-N,N-dimethylaminopropane (DSDMA); N,N-distearyl-N,N-dimethylammonium bromide (DDAB); 3-(N-(N',N'-dimethylaminoethane)-carbamoyl)cholesterol (DC-Chol); N-(1,2-dimyristyloxyprop-3-yl)-N,N-dimethyl-N-hydroxyethyl ammonium bromide (DMRIE); 2,3-dioleyloxy-N-[2(spermine-carboxamido)ethyl]-N,N-dimethyl-1-propanaminiumtrifluoroacetate (DOSPA); dioctadecylamidoglycyl spermine (DOGS); 3-dimethylamino-2-(cholest-5-en-3-beta-oxybutan-4-oxy)-1-(cis,cis-9,12-octadecadienoxy)propane (CLinDMA); 2-[5'-(cholest-5-en-3-beta-oxy)-3'-oxapentoxy)-3-dimethyl-1-(cis,cis-9',1-2'-octadecadienoxy)propane (CpLinDMA); N,N-dimethyl-3,4-dioleyloxybenzylamine (DMOBA); 1,2-N,N'-dioleyl-carbamyl-3-dimethylaminopropane (DOcarbDAP); 1,2-N,N'-dilinoleylcarbamyl-3-dimethylaminopropane (DLincarbDAP); and combinations thereof. Some positively charged lipids have a pKa at or near physiological pH and are cationic in mild acid conditions and weakly cationic at physiological pH. Such ionizable cationic lipids include, but are not limited to, ((2-((2-(dimethylamino)ethyl)thio)acetyl)

azonediyl)bis(ethane-2,1-diyl) ditetradecanoate ("S104"); (Z)-((3-(dimethylamino)propanoyl)azonediyl)bis(ethane-2,1-diyl) dioleate ("i-Et-DODC"); N-(2,3-dioleyloxy)propyl) N,N-dimethylammonium chloride ("DODMA"); 1,2-dioleoyl-3-dimethylammonium-propane ("DODAP"); and combinations thereof. Further, a suitable cationic lipid can be formed by attachment of a cationic modification group to the head group of any neutral lipid, or by attachment of a modification group that, when attached to the head group of any neutral lipid, is cationic at or near physiological pH. In some embodiments, the cationic lipid comprises a quaternary ammonium lipid. In some embodiments, the cationic lipid comprises 1,2-dioleoyl-3-trimethylammonium-propane (DOTAP).

The cationic agent can comprise an aromatic amine. The aromatic amine can be a monoamine, diamine, triamine, or quaternary amine. The aromatic amine can, in some embodiments, be carboxylated. In some embodiments, the aromatic amine comprises methotrexate.

The therapeutic agent, in some embodiments, is associated with the cationic agent in a complex that restricts access to the therapeutic agent. The cationic agent encapsulates the therapeutic agent, for example by forming a layer of cationic agents covering the therapeutic agent. In some embodiments, a single complex comprises one therapeutic agent encapsulated within the cationic agent. In some embodiments, a single complex comprises more than one therapeutic agent (e.g., two, three, or a plurality of therapeutic agents) encapsulated within the cationic agent. Because complex formation can reduce access to the therapeutic agent, formation of such a complex reduces release, and thereby toxicity, of the therapeutic agent.

The therapeutic agent can include any therapeutic agent capable of forming a complex with a cationic agent. For instance, the therapeutic agent can be a small molecule or pharmaceutical, amino acid or polypeptide, nucleic acid or polynucleotide, lipid, carbohydrate, glycolipid, polymer, metal or metal alloy, etc.

Optionally, the therapeutic agent is a polynucleotide. Non-limiting examples of polynucleotides include nucleic acids (e.g., adenine, cytosine, guanine, thymine, and uracil) and synthetic or modified nucleic acids, genes, exons, introns, oligonucleotides, plasmids, messenger RNA (mRNA), transfer RNA (tRNA), ribosomal RNA (rRNA), small-interfering RNA (siRNA), microRNA (miRNA), small nuclear RNA (snRNA), small nucleolar RNA (snoRNA), CRISPR RNA (crRNA), non-coding RNA (ncRNA), single stranded RNA or DNA (ssRNA, ssDNA), double stranded RNA (dsRNA, dsDNA), complementary DNA (cDNA), mitochondrial DNA (mtDNA), etc. Optionally, the therapeutic agent is a ribonucleic acid. Optionally, the therapeutic agent is a double-stranded ribonucleic acid. Optionally, the therapeutic agent is a siRNA. In some embodiments, the therapeutic agent is anti-TNF-α siRNA. Optionally, the anti-TNF-α siRNA has a sequence identical to SEQ ID NO: 1.

Optionally, the therapeutic agent is a small molecule. Optionally, the therapeutic agent is a small, hydrophilic molecule having in vivo toxicity. Optionally, the therapeutic agent is a small, hydrophilic molecule approved by the Food and Drug Administration (FDA) for human or veterinary administration. Suitable therapeutic agents comprising small molecules include, but are not limited to, doxorubicin, daunorubicin, cisplatin, fluorouracil, tamoxifen, carboplatin, navelbine, paclitaxel, gemcitabine, fludarabine, taxotere, goserelin, ketoconazole, methotrexate, cyclophosphamide, vincristine, leucovorin, bleomycin, camptothecin, topotecan, anthracyclines, docetaxel, didanosine, stavudine, antisense oligonucleotides, antibodies (e.g., herceptin), immunotoxins, hydroxyurea, melphalan, chlormethine, extramustinephosphate, uramustine, ifosfamide, mannomustine, trifosfamide, streptozotocin, mitobronitol, mitoxantrone, cytarabine, tegafur, idoxide, daunomycin, amphotericin (e.g., amphotericin B), mitomycin, etopside, histermine dihydrochloride, cytoxan, oxaliplatin, irinotecan, 5-irinotecan, raltitrexed, epirubicin, anastrozole, proleukin, sulindac, erthroxylaceae, cerubidine, thioguanine, fludarabine, cladribine, cytarabine, melphalan, chlorambucil, mechlorethamine, ifosfamide, triazenes, hydroxyurea, mitomycin, actinomycin, celecoxib, cetuximab, dactinomycin, levamisole, mercaptopurine, quinacrine, streptozocin, nedaplatin, satraplatin, temozolomide, mechlorethamine, melphalan, nitrosurea, plicomycin, procarbazine, raloxifene, antimicrobials (e.g., acyclovir, albendazole, amantadine, amikacin, amoxicillin, ampicillin, aztreonam, azithromycin, bacitracin, bactrim, Batrafen®, bifonazole, carbenicillin, caspofungin, cefaclor, cefazolin, cephalosporins, cefepime, ceftriaxone, cefotaxime, chloramphenicol, cidofovir, clarithromycin, clavulanic acid, clotrimazole, cloxacillin, doxycycline, econazole, erythrocycline, erythromycin, flagyl, fluconazole, flucytosine, foscarnet, furazolidone, ganciclovir, gentamycin, imipenem, isoniazid, itraconazole, kanamycin, ketoconazole, lincomycin, linezolid, meropenem, miconazole, minocycline, naftifine, nalidixic acid, neomycin, netilmicin, nitrofurantoin, nystatin, oseltamivir, oxacillin, paromomycin, penicillin, pentamidine, piperacillin-tazobactam, rifabutin, rifampin, rimantadine, streptomycin, sulfamethoxazole, sulfasalazine, tetracycline, tioconazole, tobramycin, tolciclate, tolnaftate, trimethoprim sulfamethoxazole, valacyclovir, vancomycin, zanamir, and zithromycin), steroids (e.g., betamethasone, prednisone, dexamethasone, cortisone, hydrocortisone, methylprednisolone, prednisolone, etc., and combinations thereof. The ratio of cationic agent to therapeutic agent can influence the properties of the complex within the nanoparticle. For example, in some embodiments comprising a polynucleotide, the cationic agent can shield the negative charges on the polynucleotide phosphate backbone. In some such exemplary embodiments, the cationic agent is present in an amount sufficient to shield the therapeutic agent, e.g., in molar equivalence or excess of the therapeutic agent. The ratio of the cationic agent to therapeutic agent in weight percent, in some embodiments, can be at least 1.0:1, 1.2:1, 1.5:1, 1.7:1, 2.0:1, 2.5:1, 3.0:1, 3.5:1, 4.0:1, 4.5:1, 5.0:1, 6.0:1, 7.0:1, 8.0:1, 9.0:1, 10:1, 15:1, 20:1, 25:1, 30:1, 50:1, 75:1, 90:1, 100:1, 150:1, 200:1 300:1, 500:1, 1,000:1, or at least 10,000:1. The ratio of the cationic agent to therapeutic agent in weight percent can range from any of the minimum values described above to any of the maximum values described above, for example, from 1.0:1 to 10,000:1, from 5.0:1 to 1,000:1, or from 10:1 to 100:1. In some embodiments, the ratio of the cationic agent to therapeutic agent in weight percent can range from 90:1 to 200:1.

The nanoparticle also contains a lipid core. Thus, the nanoparticle can be referred to herein as a lipid-based nanoparticle. The nanoparticle is also referred to herein as a small lipid nanoparticle (SLN). The lipid core comprises a sterol. In some embodiments, the sterol has net neutral or negative polarity or charge. In some embodiments, the lipid core further comprises an anionic or neutral lipid. The net neutral or negative polarity or charge of the sterol, and if included, the anionic or neutral lipid, is primarily responsible for an overall net neutral or negative polarity or charge of the lipid core encapsulating the complex containing the cationic agent and a therapeutic agent. Studies have shown that positively charged nanoparticles can be toxic in vivo. Thus, where the particles are administered to a subject, it can be advantageous to use non-toxic anionic or neutral sterols and/or lipids, for example, lecithin and/or cholesterol.

The therapeutic agent is substantially or essentially encapsulated within the cationic agent, thereby forming a complex, and the complex is in turn encapsulated within the lipid core. Optionally, the lipid core contains one complex. Optionally, the lipid core contains more than one complex (e.g., two, three, or a plurality of complexes). In embodiments in which the lipid core contains or encapsulates more than one complex, the complexes can be dispersed throughout the lipid core. The dispersion can be homogenous or heterogenous. Alternatively, aggregates of complexes can be encapsulated in the lipid core. As a non-limiting example, the lipid core can encapsulate five complexes, wherein all five complexes are homogenously or heterogeneously dispersed throughout the lipid core, some (e.g. two) complexes are dispersed throughout the lipid core while others (e.g., three) are aggregated together in a clump within the lipid core, or all five complexes are aggregated together in a clump within the lipid core.

The entire complex is encapsulated within the lipid core. Thus, the therapeutic agent forms a complex with a cationic agent (e.g., the therapeutic agent is encapsulated within a layer of cationic agent molecules), and the complex in turn is encapsulated within a lipid core containing a sterol. Typically, the sterol has a net neutral or negative polarity or charge. In some embodiments, the lipid core further comprises an anionic or neutral lipid. Without wishing to be bound by any one theory, it is proposed that a polar or charged, hydrophilic therapeutic agent can be compartmentalized in a lipid nanoparticle which slowly releases the therapeutic agent by first coating or masking the polar or charged portions of the therapeutic agent with a cationic agent, thereby blocking access to the therapeutic agent. This can be advantageous where, as in the example of siRNA, the therapeutic agent is highly negatively charged and unlikely to be directly encapsulated by anionic or neutral sterols and/or lipids. The cationic agent, which can cause toxicity in vivo, can then be shielded by encapsulating the complex in less toxic, anionic or neutral sterols and/or lipids. In this spatial arrangement, the sterol and, if included, the anionic or neutral lipid of the lipid core are substantially inaccessible to the therapeutic agent within the complex. Thus, the lipid core blocks access of the complex to outside influence (e.g., cells and/or cell mediators such as surface associated membrane receptors), while the cationic agent of the complex further blocks access (of even the lipid core) to the therapeutic agent. As such, the lipid core and the cationic agents of the complex, separately and collectively, act as barriers to release of the therapeutic agent. Therefore, the lipid core and the complex contribute to delaying, slowing, and/or inhibiting release of the therapeutic agent (thereby decreasing the burst rate), and reducing in vivo toxicity of the therapeutic agent. Collectively, the lipid core can be characterized by the complex functions to at least to reduce the burst rate, reduce the degradation rate of the therapeutic agent, reduce toxicity, and deliver a therapeutic agent to a subject.

The lipid core comprises a sterol. In some embodiments, the sterol comprises a phytosterol (e.g., β-sitosterol, capesterol, stigmasterol). In some embodiments, the sterol comprises ergosterol. In some embodiments, the sterol comprises a zoosterol, particularly cholesterol or derivatives thereof such as cholestanol, cholestanone, cholestenone, coprostanol, cholesteryl-2'-hydroxyethyl ether, cholesteryl-4'-hydroxybutyl ether, and combinations thereof. The lipid core can comprise more than one sterol, for example at least two sterols, at least three sterols, etc.

The lipid core comprising a sterol can further comprise an anionic lipid or a neutral lipid. In some embodiments, the lipid core can contain mixtures of anionic lipids, neutral lipids, or both anionic lipids and neutral lipids. For example, the lipid core can contain at least two, at least three, at least four, at least five, or more anionic or neutral lipids, or combinations thereof. In some embodiments, the lipid core can contain non-specific mixtures or biological extracts which primarily contain anionic and/or neutral lipids, for example lecithin. In some such embodiments, minor amounts (e.g., 20 weight percent or less) of cationic agents, cationic lipids, or other cationic molecules can be present so long as the overall net polarity or charge of the surface of the lipid core is anionic or neutral.

The anionic lipid can be any lipid having a net negative polarity or charge at or near physiological pH and capable of encapsulating a complex comprising a cationic agent and a therapeutic agent. The anionic lipid can vary in head group composition, acyl chain composition and length, degree of polarity or charge, attachment or substitution of functional groups, degree of saturation or branching of acyl chain hydrocarbons, and other features.

Suitable anionic lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG). Representative examples of phospholipids include, but are not limited to, phosphatidylcholine, phosphatidylethanolamine, phosphatidylserine, phosphatidylinositol, phosphatidic acid, palmitoyloleoyl phosphatidylcholine, lysophosphatidylcholine, lysophosphatidylethanolamine, dipalmitoylphosphatidylcholine, dioleoylphosphatidylcholine, distearoylphosphatidylcholine ordilinoleoylphosphatidylcholine. Further, a suitable anionic lipid can be formed by attachment of an anionic modification group to the head group of any neutral lipid, or by attachment of a modification group that, when attached to the head group of any neutral lipid, is anionic at or near physiological pH. In some embodiments, the anionic lipid comprises a phospholipid. In some embodiments, the anionic lipid comprises lecithin.

The neutral lipid can be any lipid having a net uncharged or zwitterionic state at or near physiological pH and capable of encapsulating a complex comprising a cationic agent and a therapeutic agent. The neutral lipid can vary in head group composition, acyl chain composition and length, degree of polarity or charge, attachment or substitution of functional groups, degree of saturation or branching of acyl chain hydrocarbons, and other features.

Suitable neutral lipids include, but are not limited to, phospholipids, aminolipids and sphingolipids, diacylphosphatidylcholine, diacylphosphatidylethanolamine, ceramide, sphingomyelin, cephalin, cerebrosides, diacylglycerols, and combinations thereof.

In some embodiments, lipid core comprises a sterol and an anionic lipid. Optionally, the lipid core comprises a sterol and a combination of phospholipids. Optionally, the lipid core comprises a sterol, particularly cholesterol, and lecithin.

The lipid core comprises a sterol and encapsulates a complex. The ratio of sterol and, if included, anionic or neutral lipid to complex can influence the properties of the nanoparticle. Specifically, the ratio of sterol and, if included, anionic or neutral lipid to cationic agent used to form the complex can influence the properties of the nanoparticle. The ratio of sterol and, if included, anionic or neutral lipid to cationic agent in weight percent, in some embodiments, can be at least 1.0:1, 1.2:1, 1.5:1, 1.7:1, 2.0:1, 2.5:1, 3.0:1, 3.5:1, 4.0:1, 4.5:1, 5.0:1, 6.0:1, 7.0:1, 8.0:1, 9.0:1, 10:1, 15:1, 20:1, 25:1, 30:1, 50:1, 75:1, or at least 100:1. The ratio of the sterol and, if included, anionic or neutral lipid to cationic agent in weight percent can range from any of the minimum values described above to any of the maximum values described above, for example, from 1.0:1 to 100:1, from 5.0:1 to 50:1, or from 10:1 to 20:1.

In some embodiments, the weight percent ratio of anionic lipid to cationic agent ranges from 10.0:1 to 1.0:1, from 5.0:1.0 to 1.0:1, from 4.0:1.0 to 1.0:1, from 3.0:1.0 to 1.0:1, from 2.5:1.0 to 1.0:1, from 2.0:1.0 to 1.0:1, or from 1.5:1.0 to 1.0:1. In some embodiments, the weight percent ratio of anionic lipid to cationic agent is about 2.1:1.

In some embodiments, the weight percent ratio of sterol or neutral lipid to cationic agent ranges from 10.0:1 to 1.0:1, from 5.0:1.0 to 1.0:1, from 4.0:1.0 to 1.0:1, from 3.0:1.0 to 1.0:1, from 2.5:1.0 to 1.0:1, from 2.0:1.0 to 1.0:1, or from 1.5:1.0 to 1.0:1. In some embodiments, the weight percent ratio of sterol or neutral lipid to cationic agent is about 1.1:1.

In some embodiments which include an anionic lipid, the weight percent ratio of anionic lipid to sterol ranges from 10.0:1 to 1.0:1, from 5.0:1.0 to 1.0:1, from 4.0:1.0 to 1.0:1, from 3.0:1.0 to 1.0:1, from 2.5:1.0 to 1.0:1, from 2.0:1.0 to 1.0:1, or from 1.5:1.0 to 1.0:1. In some embodiments, the weight percent ratio of anionic lipid to sterol is about 2.0:1. It is understood that the weight percent ratio of anionic lipid to sterol can influence the physical and chemical properties of the lipid core. For example, in embodiments in which the anionic lipid comprises lecithin and the sterol comprises cholesterol, inclusion of lecithin facilitates formation of a more pliable, spongy lipid core whereas inclusion of cholesterol increases the rigidity of the lipid core.

The lipid core encapsulates the complex comprising the cationic agent and the therapeutic agent. The lipid core can encapsulate only a few complexes (e.g., one, two, or three complexes) or a plurality of complexes. In some or further embodiments, the lipid core can encapsulate two or more different complexes. As an example, the lipid core can encapsulate at least one complex comprising a polynucleotide and at least one complex comprising a small molecule.

Optionally, the nanoparticle can further contain a polymeric molecule attached to the outer surface of the lipid core. For example, studies have shown that in vivo circulation time of nanoparticles such as liposomes increases if the particles are coated with a layer of polyethylene glycol (PEG). The PEG molecules can be attached to the lipid core by a wide array of methods. Suitable, non-limiting methods include covalent attachment via a linker (e.g., covalent linkage between the PEG molecule and the anionic or neutral lipid of the lipid core). Alternatively, the PEG molecules can be attached to the lipid by non-covalent means. For example, the PEG can insert into the lipid core by hydrophobic interaction.

In some embodiments, the nanoparticle contains a PEG layer attached to the outer surface of the lipid core. The PEG can be any PEG, preferably one in which extends the in vivo circulation time of the nanoparticle. The PEG layer can comprise PEG molecules 20 kDa or less, or 15 kDa or less. Optionally, the PEG layer can comprise PEG molecules 10 kDa or less, 9 kDa or less, 8 kDa or less, 7 kDa or less, 6 kDa or less, 5 kDa or less, 4 kDa or less, 3 kDa, or less 2 kDa or less, 1 kDa or less, 0.8 kDa or less, 0.5 kDa or less, 0.3 kDa or less, or 0.1 kDa or less. Optionally, the PEG layer contains a mixture of different PEG molecules.

In some embodiments, the weight percent ratio of anionic lipid to PEG ranges from 10.0:1 to 1.0:1, from 5.0:1.0 to 1.0:1, from 4.0:1.0 to 1.0:1, from 3.0:1.0 to 1.0:1, from 2.5:1.0 to 1.0:1, from 2.0:1.0 to 1.0:1, or from 1.5:1.0 to 1.0:1. In some embodiments, the weight percent ratio of anionic lipid to PEG is about 3.2:1.

In some embodiments, the weight percent ratio of sterol to PEG ranges from 10.0:1 to 1.0:1, from 5.0:1.0 to 1.0:1, from 4.0:1.0 to 1.0:1, from 3.0:1.0 to 1.0:1, from 2.5:1.0 to 1.0:1, from 2.0:1.0 to 1.0:1, or from 1.5:1.0 to 1.0:1. In some embodiments, the weight percent ratio of sterol to PEG is about 1.6:1.

In some embodiments, the weight percent ratio of cationic agent to PEG ranges from 10.0:1 to 1.0:1, from 5.0:1.0 to 1.0:1, from 4.0:1.0 to 1.0:1, from 3.0:1.0 to 1.0:1, from 2.5:1.0 to 1.0:1, from 2.0:1.0 to 1.0:1, or from 1.5:1.0 to 1.0:1. In some embodiments, the weight percent ratio of cationic agent to PEG is about 1.5:1.

Optionally, the nanoparticle can contain a targeting molecule to facilitate targeting of the nanoparticle to specific areas in vivo. The targeting molecule targets the nanoparticle to a particular tissue or cell type by specifically binding a ligand present in that tissue or cell type, or by being specifically altered by a cell, molecule, or condition present in that particular tissue or cell type. The targeting molecule can be any peptide, polypeptide, nucleic acid, polynucleotide, carbohydrate, lipid, small molecule, or synthetic molecule. For example, an antibody can target the nanoparticle to a cell type having a ligand to which the antibody specifically binds. Antibody targeting molecules can be polyclonal, monoclonal, fragments, recombinant, or single chain, many of which are commercially available or readily obtained using standard techniques. A targeting molecule can be attached to the lipid core via, for example, a hydrophobic linker which associates with the lipid core, or via linkage (e.g., covalently) with a surface molecule (e.g., PEG molecule).

Optionally, the targeting molecule is a PEG molecule in the PEG layer. The PEG molecule can be responsive to particular environments or conditions. For example, the PEG molecule can contain an acid-sensitive linker. When the PEG molecule containing an acid-sensitive linker is exposed to slightly acidic conditions (e.g., pH 6.8 or less), the acid-sensitive linker is hydrolyzed. Hydrolysis of the acid-sensitive linker releases the cleaved portion of the PEG molecule from the nanoparticle. After release of the PEG molecule, the in vivo circulation time of the nanoparticle decreases. By this exemplary mechanism, the nanoparticle can be targeted to specific pH (e.g., acidic) environments, for instance inflammatory sites containing a local pH of 6.8 or less. Similar mechanisms can also be used to target the nanoparticles to e.g., environments containing particular hypoxic, tumor, temperature, or redox statuses, or environments containing a particular biomolecule target.

Optionally, the nanoparticle can contain one or more additional components. The additional component can include a component which, for example, enhances, synergizes or has additive effects with, or otherwise complements the function of the therapeutic agent. Alternatively, the additional component can treat a condition that is the same as or associated with the condition the therapeutic agent is intended to treat. Alternatively, the additional component can treat and/or prevent a side-effect caused by administration of the therapeutic agent. For example, the nanoparticle can contain an anti-inflammatory compound, particularly a corticosteroid, as an additional component. Inclusion of a corticosteroid, particularly a glucocorticoid, can in some embodiments prevent acute inflammatory responses induced by the therapeutic agent, particularly double-stranded RNA such as siRNA. Suitable corticosteroids include hydrocortisone, cortisone, ethamethasoneb, prednisone, prednisolone, triamcinolone, methylprednisolone, betamethasone, dexamethasone, and fludrocortisone. Optionally, the lipid core comprises betamethasone.

The herein disclosed nanoparticles have numerous advantageous properties, including but not limited to, desirable size, polydispersity index (PDI), zeta potential, encapsulation efficiency, burst release, and overall charge.

The nanoparticle can have a diameter within the nanometer range (e.g., from 1 to 1,000 nm). In some embodiments, the nanoparticle has a diameter of 1,000 nm or less, 500 nm or less, 300 nm or less, or 200 nm or less. In some embodiments, the nanoparticle has a diameter from 10 to 500 nm. Optionally, the nanoparticle has a diameter from 10 to 300 nm, from 25 to 250 nm, from 40 to 200 nm, or from 50 to 180 nm. Nanoparticles formulated for non-ingested and non-injected administration (e.g., topical administration) can have a diameter larger than the nanometer range (e.g., from greater than 1,000 nm to 10,000 nm).

The nanoparticle can have a polydispersity index (PDI) of less than 0.8, as measured by dynamic light scattering methods. In some embodiments, the nanoparticle has a PDI of less than 0.6, less than 0.5, less than 0.4, less than 0.3, or less than 0.2, as measured by dynamic light scattering methods.

The nanoparticle can have a zeta potential of ±5 mV or more, as measured by dynamic light scattering methods. In some embodiments, the nanoparticle has a zeta potential of ±10 mV or more, ±15 mV or more, ±20 mV or more, ±25 mV or more, ±30 mV or more, ±40 mV or more, ±50 mV or more, or ±60 mV or more, as measured by dynamic light scattering methods.

The nanoparticle can have an encapsulation efficiency of greater than 50% of the therapeutic agent. In some embodiments, the nanoparticle has an encapsulation efficiency of greater than 60%, greater than 70%, greater than 80%, greater than 90%, greater than 92%, greater than 95%, greater than 97%, or greater than 99% of the therapeutic agent. The term "encapsulation efficiency," as used herein, refers to the percentage of therapeutic agent provided in a mixture with the cationic agent that is encapsulated by nanoparticles formed from the complex comprising a therapeutic agent and cationic agent.

The nanoparticle can have an advantageous burst release, as defined by the percentage of therapeutic agent released from the nanoparticle in phosphate-buffered saline (PBS) at pH 7.4 within 30 days from nanoparticle formation. The term "burst release" can be used to characterize the nanoparticle or the therapeutic agent within the nanoparticle. For example, a nanoparticle can be said to have a burst release of a therapeutic agent of 20% or less within 30 days. Alternatively, a therapeutic agent can be said to have a burst release from a nanoparticle of 20% or less within 30 days. The nanoparticle can have a burst release of 50% or less, 40% or less, 30% or less, 20% or less, 10% or less, 7% or less, 5% or less, 3% or less, or 2% or less within 30 days from nanoparticle formation.

The nanoparticle can have an advantageous overall charge. In some embodiments, the nanoparticle has an overall neutral charge. In some embodiments, the nanoparticle has an overall negative charge.

Optionally, the nanoparticle can be formulated in a medicament. The nanoparticle can be formulated in any suitable medicament including, for example, but not limited to, solids, semi-solids, liquids, and gaseous (inhalant) dosage forms, such as tablets, pills, powders, liquid solutions or suspensions, suppositories, injectables, infusions, inhalants, hydrogels, topical gels, sprays, and the like. Optionally, the medicament comprises a pharmaceutically acceptable excipient. Optionally, the medicament comprises an effective dose of the therapeutic agent.

Methods of Preparing Lipid-Based Nanoparticle Compositions

Also disclosed herein are methods to produce a nanoparticle. The methods are advantageous at least because they result in particles having 1) high agent encapsulation efficiency, 2) minimal therapeutic agent burst release, 3) small diameters (e.g., about 130 nm), which are ideal for targeted delivery of agents to, e.g., tumors and chronic inflammation sites, and 4) negative zeta potential, indicating high stability and less toxicity in vitro and in vivo. Further, the methods do not require a change in pH, thereby facilitating use of pH-sensitive materials in the particles.

Disclosed herein is a method of producing a nanoparticle, comprising: a) combining a cationic agent, a therapeutic agent, and a first water-immiscible solvent with a first aqueous solution, thereby forming a mixture comprising a complex comprising the cationic agent and the therapeutic agent; b) combining the mixture with a second water-immiscible solvent, thereby forming an aqueous phase and an organic phase, and separating the organic phase comprising the complex; c) combining the organic phase comprising the complex with a sterol and a first water-miscible organic solvent; and d) dispersing the complex in a second aqueous solution to form a nanoparticle comprising a lipid core comprising a sterol; and a complex comprising a cationic agent and a therapeutic agent, wherein the complex is encapsulated within the lipid core.

The methods can include any herein disclosed cationic agent, sterol, and, if included, any anionic lipid or neutral lipid. The methods can further include any herein disclosed therapeutic agent.

The method includes a water-immiscible solvent. A water-immiscible solvent is a solvent that is liquid at room temperature and does not readily form a homogenous mixture with water at ambient conditions. Numerous water-immiscible solvents are known in the art. Non-limiting examples of suitable water-immiscible solvents include substituted or unsubstituted, linear, branched or cyclic alkanes, alkenes, or alkynes; aromatic hydrocarbons; organic solvents, completely or partially halogenated hydrocarbons, ethers, esters (e.g., dibasic or emollient esters), ketones, mono-, di- or tri- glycerides, native oils, alcohols, aldehydes, acids, amines, linear or cyclic silicones, hexamethyldisiloxane, carbon tetrachloride, methylene chloride, chloroform, tetrachloroethylene, trichloroethylene, trichloroethane, hydrofluorocarbons, chlorinated benzene (mono, di, tri), trichlorofluoromethane, diethyl ether, toluene, xylene, ethyl acetate, dichloroethane, n-butylacetate, cyclohexane, 1,2-dichloroethane, dichloromethane, diethyl ether, dimethyl formamide, ethyl acetate, heptane, hexane, methyl-tert-butyl ether, pentane, toluene, 2,2,4-trimethylpentane, dimethyl formamide, methyl-tert-butyl ether, pentane, etc., and mixtures thereof.

In some embodiments, the method includes one or more water-immiscible solvents (e.g., a first water-immiscible solvent and a second water-immiscible solvent). In some embodiments, the method includes numerous water-immiscible solvents (e.g., a first, second, and a third or more water-immiscible solvents). The water-immiscible solvents can be any water-immiscible solvents disclosed herein. Optionally, any one or more water-immiscible solvents are the same. Optionally, all water-immiscible solvents are the same. In some embodiments, the water-immiscible solvent is a chloromethane. In some embodiments, the water-immiscible solvent is selected from chloroform and dichloromethane.

The method includes a water-miscible solvent. A water-miscible solvent is a solvent that is liquid at room temperature and readily forms a homogenous mixture with water at ambient conditions. Numerous water-miscible solvents are known in the art. Non-limiting examples of suitable water-miscible solvents include acetaldehyde, acetic acid, acetone, acetonitrile, benzyl alcohol, butanediol, butoxyethanol, butyric acid, diethanolamine, diethylenetriamine, dimethylformamide, dimethoxyethane, dimethyl sulfoxide, dioxane, ethanol, ethylamine, ethyl acetate, ethylene glycol, formic acid, furfuryl alcohol, glycerol, methanol, methyl diethanoloamine, methyl isocyanide, propanol, propanediol, pentanediol, propanoic acid, propylene carbonate, propylene glycol, pyridine, tetrahydrofuran (THF), triethylene glycol, water, etc., and mixtures thereof.

In some embodiments, the method includes one or more water-miscible solvents (e.g., a first water-miscible solvent and a second water-miscible solvent). In some embodiments, the method includes numerous water-miscible solvents (e.g., a first, second, and a third or more water-miscible solvents). Optionally, any one or more water-miscible solvents are the same. Optionally, all water-miscible solvents are the same. In some embodiments, the water-miscible solvent is an alcohol. In some embodiments, the water-miscible solvent is selected from methanol and ethanol. In some embodiments, the water-miscible solvent is a cyclic ether. In some embodiments, the water-miscible solvent is tetrahydrofuran (THF).

The combining steps can be performed by any method useful to combine the recited components. For example, the components can be combined by adding, pouring, titrating, mixing, dissolving, injecting, etc. A first component can be combined by addition to a second component, or vice versa. Alternatively, numerous components can be combined with each other or into another component. Optionally, any one or more combining steps are performed while stirring or mixing the components (e.g., stirring via a stir bar at 1,000 rpm in a fume or chemical hood).

In the method, step a) includes combining a cationic agent, a therapeutic agent, and a first water-immiscible solvent with a first aqueous solution, thereby forming a mixture comprising a complex comprising the cationic agent and the therapeutic agent. Typically, the cationic agent is dissolved in the first water-immiscible solvent prior to addition to the aqueous solution. Optionally, the first water-immiscible solvent is a chloromethane, particularly chloroform. Optionally, the total amount of cationic agent present in the first aqueous solution is 100 mg/mL or less. Optionally, the total amount of cationic agent present in the first aqueous solution is 50 mg/mL or less, 25 mg/mL or less, 10 mg/mL or less, 5 mg/mL or less, 4 mg/mL or less, 3 mg/mL or less, 2.5 mg/mL or less, 2 mg/mL or less, 1.5 mg/mL or less, 1.25 mg/mL or less, 1 mg/mL or less, 0.5 mg/mL or less, or 0.1 mg/mL or less.

In some embodiments, the therapeutic agent is dissolved in the first aqueous solution. Optionally, the first aqueous solution is purified and/or distilled water. In some or further embodiments, the first aqueous solution is RNase-free water. Optionally, the total amount of therapeutic agent present in the first aqueous solution is 1 mM or less. Optionally, the total amount of therapeutic agent in the first aqueous solution is 100 $\mu$M or less, 50 $\mu$M or less, 25 $\mu$M or less, 10 $\mu$M or less, 5 $\mu$M or less, 4 $\mu$M or less, 3 $\mu$M or less, 2 $\mu$M or less, or 1 $\mu$M or less.

In some or further embodiments, the method further includes mixing the components of step a) until an emulsion is created. Any means of mixing the components can be performed. For example, the components can be sonicated to achieve dispersion of the complexes in the aqueous solution. The emulsion may appear milky.

In some or further embodiments, the method further includes combining the mixture with a second water-miscible organic solvent. Inclusion of this step before performing step b) can facilitate complex formation. Typically, when this step is performed, a sufficient amount of the second water-miscible organic solvent should be added to result in a monophase solution. Optionally, the second water-miscible organic solvent is an alcohol. Optionally, the second water-miscible organic solvent is methanol.

In the method, step b) includes combining the mixture with a second water-immiscible solvent, thereby forming an aqueous phase and an organic phase, and separating the organic phase comprising the complex. A sufficient amount of the second water-immiscible solvent should be added to result in phase separation of an organic phase and an aqueous phase. In some embodiments, about an equal volume of the second water-immiscible solvent is added to the mixture. Optionally, the second water-immiscible solvent is a chloromethane, particularly chloroform. This step results in separation of the complexes formed in step a) into the organic phase.

The organic phase comprising the complex can be separated from the aqueous phase by any method known in the art. For example, one phase can be poured off, pipetted out, drained through a separatory funnel, or separated by other methods. The organic phase contains most of the complexes formed in step a). The aqueous phase can be discarded.

In the method, step c) includes combining the organic phase comprising the complex with a sterol and a first water-miscible organic solvent. In embodiments in which the lipid core further comprises an anionic and/or neutral lipid, step c) is modified to include combining the organic phase comprising the complex with a sterol, the anionic and/or neutral lipid, and a first water-miscible organic solvent. Typically, the sterol is dissolved in a water-immiscible solvent (e.g., a third water-immiscible solvent) prior to combining the first water-miscible organic solvent. Optionally, the third water-immiscible solvent is the same as the second water-immiscible solvent used in step b). Optionally, the water-immiscible solvent is a chloromethane, particularly chloroform.

In some embodiments, the sterol and, if included, the anionic or neutral lipid, is combined directly (e.g., added drop-wise or titrated) into the organic phase obtained in step b). In such embodiments, it can be advantageous if the second and third water-immiscible solvents are the same solvents.

In some or further embodiments, at least a portion of the water-immiscible solvent(s) present in the organic phase are removed before combining the first water-miscible organic solvent. For example, the water-immiscible solvent(s) can be evaporated under inert gas (e.g., nitrogen gas). The water-immiscible solvent(s) can be removed prior to, during, or after combining the sterol and, if included, the anionic or neutral lipid. Removal of water-immiscible solvent(s) can facilitate dispersion of nanoparticles in subsequent steps. Optionally, essentially all of the water-immiscible solvent(s) are removed such that a dried lipid layer containing the cationic agent-therapeutic agent complex remains. It is understood that even under the most thorough drying methods, residual water-immiscible solvent(s) can remain.

Optionally, the total amount of sterol (and, if included, anionic or neutral lipid) present in the organic phase solution is 100 mg/mL or less. Optionally, the total amount of sterol present in the organic phase solution is 50 mg/mL or less, 25 mg/mL or less, 16 mg/mL or less, 10 mg/mL or less, 8 mg/mL or less, 5 mg/mL or less, 4 mg/mL or less, 3 mg/mL or less, 2.5 mg/mL or less, 2 mg/mL or less, 1 mg/mL or less, 0.5 mg/mL or less, or 0.1 mg/mL or less.

Step c) includes combining the organic phase comprising the complex with a sterol. Optionally, one anionic lipid, one neutral lipid, or both one anionic lipid and one neutral lipid are further included. Optionally, one or more sterols and either one or more anionic lipids, or one or more neutral lipids, or both one or more anionic lipids and one or more neutral lipids are included. Where more than one lipid (e.g. of one or either type of anionic or neutral lipid) is included, the lipids can be combined with the sterol in the organic phase separately or together. In some embodiments, one or more types of lipids are combined with the sterol in a water-immiscible solvent prior to addition to the organic phase comprising the complex.

In some or further embodiments, a polymeric molecule can be combined with the organic phase comprising the complex. For example, PEG molecules can be combined with the organic phase along with, or at about the same time as, the sterol. A sufficient amount of PEG molecules can be combined to form a PEG layer on the nanoparticles effective to increase the in vivo circulation time of the nanoparticles. In some embodiments, the PEG molecule comprises an acid-sensitive linker.

In some or further embodiments, one or more additional components can be combined with the organic phase comprising the complex. The additional component can include any additional component disclosed herein, for example, an anti-inflammatory compound, particularly a corticosteroid. Inclusion of a corticosteroid, particularly a glucocorticoid, can in some embodiments prevent acute inflammatory responses induced by the therapeutic agent, particularly double-stranded RNA such as siRNA. Optionally, betamethasone is combined with the organic phase comprising the complex.

Step c) includes combining the organic phase comprising the complex, a sterol, and a first water-miscible organic solvent. It is important that the solvents and compositions in this step are substantially devoid of chloroform, as lipid nanoparticles in chloroform are emulsion-based, which typically have higher burst release rates. In embodiments in which the water-immiscible solvent(s) are removed prior to combining the first water-miscible organic solvent, lower amounts of the first water-miscible organic solvent can be used. For example, the dried lipids and lipid-therapeutic agent complexes can be combined with only several mL or even μL amounts of the first water-miscible organic solvent.

The first water-miscible solvent can be any water-miscible solvent disclosed herein. In some embodiments, the first water-miscible solvent is a cyclic ether. In some embodiments, the first water-miscible solvent is tetrahydrofuran (THF).

In some or further embodiments, the method can include mixing the mixture of first water-miscible organic solvent and the lipids and lipid-therapeutic agent complexes. For example, the mixture can be stirred, sonicated, vortexed, inverted, etc., or combinations thereof.

In the method, step d) includes dispersing the complex in a second aqueous solution to form a nanoparticle comprising a lipid core, wherein the lipid core comprises a sterol and encapsulates a complex comprising a cationic agent and a therapeutic agent, and wherein the sterol encapsulates the complex. Optionally, the second aqueous solution is purified and/or distilled water. In some or further embodiments, the second aqueous solution is RNase-free water.

Dispersion of the complex in the second aqueous solution can be facilitated by adding the first water-miscible solvent solution (comprising lipids and lipid-therapeutic agent complexes) dropwise into a larger volume of the second aqueous solution while stirring. In some embodiments, the first water-miscible solvent is evaporated while stirring the solution. Nanoparticles form spontaneously during this step.

In some or further embodiments, the method can include collecting or concentrating the nanoparticles. The nanoparticles can be collected by, for example, centrifugation. In some or further embodiments, the nanoparticles can be washed and resuspended in desirable buffered solutions at desirable concentrations.

In some embodiments, the method can be completed without changing the temperature (e.g., the method can be completed in its entirety at ambient temperature). In some embodiments, the method further comprises removing substantially all uncomplexed siRNA.

Methods of Treating

Also disclosed herein are methods of treating a subject with a nanoparticle. The methods include treating a subject with a disease, comprising: administering to the subject a nanoparticle comprising a lipid core comprising a sterol; and a complex comprising a cationic agent and a therapeutic agent, wherein the complex is encapsulated within the lipid core. The nanoparticle can be any nanoparticle disclosed herein.

In some embodiments, the administering step can include any method of introducing the particle into the subject appropriate for the particle formulation. The administering step can include at least one, two, three, four, five, six, seven, eight, nine, or at least ten dosages. The administering step can be performed before the subject exhibits disease symptoms (e.g., prophylactically), or during or after disease symptoms occur. The administering step can be performed prior to, concurrent with, or subsequent to administration of other agents to the subject. The administering step can be performed with or without co-administration of additional agents (e.g., immunosuppressive agents).

The subject can be any mammalian subject, for example a human, dog, cow, horse, mouse, rabbit, etc. In some embodiments, the subject is a primate, particularly a human. The subject can be a male or female of any age, race, creed, ethnicity, socio-economic status, or other general classifiers.

The disease can be any disease in which administration of a nanoparticle comprising a therapeutic agent can be used to treat. In some embodiments, the disease is an inflammatory disease. In some embodiments, the disease is chronic inflammation. Non-limiting examples of inflammatory diseases include arthritis (e.g., rheumatoid arthritis, collagen antibody-induced arthritis), asthma, chronic peptic ulcer, tuberculosis, periodontitis, ulcerative colitis, Crohn's disease, sinusitis, hepatitis, bronchitis, appendicitis, dermatitis, meningitis, ankylosing spondylitis, celiac disease, idiopathic pulmonary fibrosis, lupus, systemic lupus erythematosus, psoriasis, type 1 diabetes, Addison's disease, allergy, arthritis, prostatitis, diverticulitis, glomerulonephritis, hidradenitis suppurativa, inflammatory bowel disease, interstitial cystitis, mast cell activation syndrome, mastocytosis, otitis, pelvic inflammatory disease, reperfusion injury, rheumatic fever, rhinitis, sarcoidosis, transplant rejection, vasculitis, atherosclerosis, gout, pleurisy, eczema, gastritis, splenitis, laryngitis, thyroiditis, pharyngitis, multiple sclerosis, myopathies, seborrheic dermatitis, Wegener's granulomatosis, acne vulgaris, Alzheimer's disease, autoimmune diseases, hypersensitivities, Parkinson's disease, etc., and combinations thereof.

In some embodiments, the disease is a cell-cycle regulation disorder. In some embodiments, the disease is cancer. Non-limiting examples of cancers include Acute granulocytic leukemia, Acute lymphocytic leukemia, Acute myelogenous leukemia (AML), Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma, Bile duct cancer, Bladder cancer, Bone cancer Bone marrow cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia (CLL), Chronic myelogenous leukemia (CML), Colon cancer, Colorectal cancer, Craniopharyngioma, Cutaneous lymphoma, Cutaneous melanoma, Diffuse astrocytoma, Ductal carcinoma in situ (DCIS), Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors (GIST), Germ cell tumor, Gestational Trophoblastic Disease (GTD), Glioblastoma multiforme (GBM), Glioma, Hairy cell leukemia, Head and neck cancer, Hemangioendothelioma, Hodgkin's lymphoma, Hypopharyngeal cancer, Infiltrating ductal carcinoma (IDC), Infiltrating lobular carcinoma (ILC), Inflammatory breast cancer (IBC), Intestinal Cancer, Intrahepatic bile duct cancer, Invasive/infiltrating breast cancer, Islet cell cancer, Jaw/oral cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Mycosis Fungoides, Myelodysplastic Syndrome, Nasal cavity cancer, Nasopharyngeal cancer, Neck cancer, Neuroblastoma, Neuroendocrine tumors (NETs), Non-Hodgkin's lymphoma, Non-small cell lung cancer (NSCLC), Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system (CNS) lymphoma, Prostate cancer, Rectal cancer, Renal cell carcinoma, Renal pelvis cancer, Rhabdomyosarcoma, Salivary gland cancer, Sarcoma, Sinus cancer, Skin cancer, Small cell lung cancer (SCLC), Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma, Testicular cancer, Throat cancer, Thymoma/thymic carcinoma, Thyroid cancer, Tongue cancer, Tonsil cancer, Transitional cell cancer, Transitional cell cancer, Triple-negative breast cancer, Tubal cancer, Tubular carcinoma, Ureteral cancer, Urethral cancer, Uterine adenocarcinoma, Uterine cancer, Uterine sarcoma, Vaginal cancer, Vulvar cancer, Wilms tumor, Waldenstrom macroglobulinemia, etc., and combinations thereof.

In some embodiments, the method treats the disease by delivering a nanoparticle comprising a therapeutic agent. In some embodiments, the method reduces systemic delivery of the therapeutic agent. In some embodiments, the method delivers the therapeutic agent locally to the site of the disease. Optionally, the method reduces undesirable side-effects of the therapeutic agent.

In some embodiments, the method can treat inflammation by releasing the therapeutic agent in vivo, wherein the therapeutic agent reduces pro-inflammatory mediators. In some embodiments, the therapeutic agent is anti-TNF-$\alpha$ siRNA. In some embodiments, the therapeutic agent treats inflammation by reducing expression of TNF-$\alpha$.

In some embodiments, the method can treat cancer by releasing the therapeutic agent in vivo, wherein the therapeutic agent is an anti-cancer or anti-tumor agent. In some embodiments, the therapeutic agent is a small molecule. In some embodiments, the therapeutic agent is an anthracycline. In some embodiments, the therapeutic agent is doxorubicin.

In some embodiments, the method includes treating a subject with a disease comprising administering to the subject a nanoparticle comprising a therapeutically effective dose of a therapeutic agent. The nanoparticle can be provided in the form of a medicament. The nanoparticle can further comprise a pharmaceutically acceptable excipient.

Also disclosed herein are methods of reducing the burst rate of a therapeutic agent from a nanoparticle. The methods comprise encapsulating the therapeutic agent in a nanoparticle comprising a lipid core comprising a sterol; and a complex comprising a cationic agent and a therapeutic agent, wherein the complex is encapsulated within the lipid core, wherein the burst rate of the therapeutic agent from the nanoparticle is 50 percent or less within 30 days.

The therapeutic agent can be encapsulated in a nanoparticle by any of the herein disclosed methods for preparing lipid-based nanoparticles.

In some embodiments, the therapeutic agent can have a burst release from the nanoparticle of 40% or less, 30% or less, 20% or less, 10% or less, 7% or less, 5% or less, 3% or less, or 2% or less within 30 days from nanoparticle formation.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

Therapeutic Efficacy of TNF-α siRNA-Incorporated Acid-Sensitive Sheddable PEGylated Solid Lipid Nanoparticles with High Encapsulation Efficiency & Minimum Burst Release in a Mouse Model of Arthritis.

Methods

Polyethylene glycol 2000-hydrazone-stearic acid derivative (C18) (PHC) and polyethylene glycol 2000-amide-stearic acid derivative (C18) (PAC) were synthesized following previously published methods. Cholesterol, chloroform, tetrahydrofuran (THF), Lugol's solution, Tris-EDTA (TE), sodium dodecyl sulfate, Triton X-100, N,N-dimethyl-9,9-biacridinium dinitrate (Lucigenin), and LPS from *Salmonella enterica* serotype *enteritidis* were from Sigma-Aldrich (St. Louis, Mo.). TopFluor cholesterol and 1,2-dioleoyl-3-trimethylammonium-propane (DOTAP) were from Avanti Polar Lipids (Alabaster, Ala.). Lecithin was from Alfa Aesar (Ward Hill, Mass.). BLOCK-iT™ Fluorescent Oligo siRNA was from Life Technologies (Grand Island, N.Y.). Negative control siRNA (Medium GC Duplex), Dulbecco's Modified Eagle Medium (DMEM), FBS, and streptomycin/penicillin were from Invitrogen (Carlsbad, Calif.). TNF-α siRNA (5'-GUCUCAGCCUC-UUCUCAUUCCUGCT-3') (SEQ ID NO: 1) was synthesized by Integrated DNA Technologies (Coralville, Iowa).

Preparation of siRNA-incorporated nanoparticles. A 50 μL solution of 20 uM of siRNA in TE buffer (10 mM Tris-HCl and 1 mM EDTA in water, pH 7.5) was added to 450 μL of RNase-free water. DOTAP in chloroform (1.25 mg in 680 μL) was then added drop-wise to the siRNA solution while stirring. The mixture was sonicated briefly in a water bath sonicator and mixed with 1.36 ml of methanol to form a monophase. After one hour of incubation at room temperature, the siRNA/DOTAP complexes were extracted into chloroform by phase separation.

Lecithin (3.2 mg) and cholesterol (1.6 mg), dissolved in chloroform, were added drop-wise to the siRNA/DOTAP complexes in chloroform while stirring. PHC or PAC (2 mg) dissolved in chloroform was then added drop-wise to the siRNA-lipids mixture. The resultant mixture was dried under nitrogen gas and then dissolved in 500 μL of THF, which was then added dropwise into water while stirring. Solvent was evaporated by stirring at room temperature for 6 hours. Nanoparticles were collected by centrifugation, washed, and re-suspended in diethylpyrocarbonate (DEPC)-treated water (Invitrogen). Nanoparticles prepared with PHC are named AS-siRNA-SLNs, where AS indicates that the nanoparticles are PEGylated with the acid-sensitive sheddable PEG2000 (i.e., PHC), siRNA refers to encapsulated siRNA, and SLN refers to small lipid nanoparticle. Nanoparticles prepared with PAC are named AI-siRNA-SLNs, where AI indicates that the nanoparticles were PEGylated with PAC, which is acid-insensitive. Fluorescently labeled nanoparticles were prepared by using fluorescein-labeled siRNA or TopFluor cholesterol (62.5% of total cholesterol) in the preparation.

Characterization of siRNA-incorporated nanoparticles. The particle size, polydispersity index (PDI), and zeta potential of the siRNA-incorporated nanoparticles were determined using a Malvern Zeta Sizer Nano ZS (Westborough, Mass.). To determine the encapsulation efficiency of the siRNA in the nanoparticles, nanoparticles were prepared with fluorescein-labeled siRNA to measure the florescent intensity of the unencapsulated siRNA in water phase with more than 99% of siRNA complexed with DOTAP. The fluorescence intensity was measured using a BioTek Synergy HT Multi-Mode Microplate Reader (Winooski, Vt., Ex=485 nm, Em=528 nm).

Transmission electron microscopy (TEM). The morphology of the AS-TNF-α siRNA-SLNs was examined using an FEI Tecnai Transmission Electron Microscope in the Institute for Cellular and Molecular Biology (ICMB) Microscopy and Imaging Facility at The University of Texas at Austin (Austin, Tex.). Carbon-coated 400-mesh grids were activated for 1-2 min. One drop of the nanoparticle suspension was deposited on the grids and incubated overnight at room temperature before examination.

In vitro release of siRNA from the nanoparticles. The release of siRNA from the nanoparticles was measured using nanoparticles prepared with fluorescein-labeled siRNA. About 9 mg of AS-siRNA-SLNs were suspended in 1 ml PBS (10 mM, pH 7.4) inside a dialysis bag (MWCO 50 kDa, Spectrum Laboratories, Calif.), which was then placed into 50 ml PBS (10 mM, pH 7.4) and maintained in a shaker incubator (MAQ 5000, MODEL 4350, Thermo Fisher Scientific, Waltham, Mass.) (100 rpm, 37° C.). At given time points (1, 24, 48, 96, 192, 450 and 720 h), the amount of siRNA in the release medium was measured by measuring the fluorescence intensity using a BioTek Synergy HT Multi-Mode Microplate Reader. The percent of siRNA released was calculated using the following equation: % released=100×fluorescence intensity in the release medium/total fluorescence intensity of encapsulated siRNA.

In vitro binding/uptake of siRNA-incorporated nanoparticles by macrophages. Murine macrophage J774A.1 cells (American Type Culture Collection, Manassas, Va.) were seeded in a 12-well plate ($2 \times 10^5$ cells/well). To study the effect of the acid-sensitive sheddable PEGylation of the nanoparticles on their uptake by the cells, the AS-siRNA-SLNs or AI-siRNA-SLNs were pre-incubated in PBS (200 mM, pH 6.8 or 7.4) for 6 h to facilitate the shedding of the PEG before the nanoparticles were added into the cell culture medium. After 50 min of co-incubation, the cells were washed with PBS (10 mM, pH 7.4) and lysed with a lysis solution that contained 2% (v/v) sodium dodecyl sulfate and 1% Triton X-100. The fluorescence intensity in the cell lysates was measured (Ex=485 nm, Em=528 nm).

TNF-α release from J774A.1 macrophages in culture. J774A.1 cells were seeded in 96-well plates (10,000 cells per well). After 20 h incubation at 37° C., 5% CO2, the culture medium was replaced with serum-free DMEM containing TNF-α-siRNA incorporated AS-siRNA-SLNs at a final siRNA concentration of 500 ng/ml. The culture medium was replaced 4 h later with fresh DMEM containing 10% FBS. Nineteen hours later, LPS was added into the cell culture medium to a final concentration of 100 ng/ml. The cell culture medium was harvested after five additional hours of incubation to measure TNF-α concentration using a mouse TNF-α ELISA Kit (Thermo Fisher Scientific, Waltham, Mass.).

LPS-induced mouse model of chronic inflammation. All animal studies were conducted in accordance with the U.S. National Research Council Guidelines for the care and use of laboratory animals. The animal protocol was approved by the Institutional Animal Care and Use Committee at The University of Texas at Austin. Female C57BL/6 mice (6-8 weeks) were from Charles River Laboratories (Wilmington, Mass.). For imaging, mice were fed with alfalfa-free diet (Harlan, Ind.) to minimize unwanted background signals. An LPS-induced mouse model of chronic inflammation was established according to methods known in the art. LPS was dissolved in sterile PBS (pH 7.4, 10 mM) at a concentration of 1 mg/ml. A 50 μl of the solution was injected into the right hind footpad of the mice on day 0. On day 8, chronic inflammation was confirmed using an IVIS™ Spectrum (Caliper, Hopkinton, Mass.) with a bioluminescence imaging system 20 min following intraperitoneal (i.p.) injection of lucigenin (15 mg/kg) (exposure time 60 s, large binning, field B). Lucigenin is known to react with the superoxide produced by macrophages during chronic inflammation. Mice that did not show significant chronic inflammation were excluded.

CIA model. CIA was induced in 8-12-week-old female DBA/1J mice (Taconic) with a Hooke CIA Induction Kit following the manufacturer's instructions (Hooke Laboratories, Mass.). Chicken type II collagen in an emulsion with Freund's complete adjuvant was used for initial immunization, and chicken type II collagen in an emulsion with Freund's incomplete adjuvant was used for boosting. The emulsions were intradermally injected in the base of the tail. Mice were observed daily for signs of joint inflammation.

Biodistribution studies. To evaluate the accumulation of the AI-siRNA-SLNs and AS-siRNA-SLNs in LPS-induced inflamed mouse feet, mice were i.v. injected with AI-siRNA-SLNs or AS-siRNA-SLNs (labeled with TopFluor cholesterol, 0.2 mg/kg), and the inflamed foot (i.e., right hind) was imaged using IVIS™ Spectrum at 6 hrs and 24 hrs after the injection. As controls, mice were i.v. injected with sterile PBS. Mice were euthanized 24 hrs later to collect inflamed foot and major organs (i.e., heart, kidneys, liver, spleen, and lung). All samples were then imaged using an IVIS™ Spectrum (Ex=495 nm, Em=507 nm). In another study, CIA mice were i.v. injected with PBS, free siRNA, or AS-siRNA-SLNs (siRNA was fluorescently-labeled, 0.5 mg siRNA/kg). Mouse joints were imaged using IVIS™ Spectrum 24 and 48 hrs after the injection (Ex=485 nm, Em=528 nm). All the fluorescent units are in photons per second per centimeter square per steradian (p/s/cm²/sr).

CAIA model and siRNA treatment. CAIA was induced in 8-12-week-old male BALB/c mice (Charles River Laboratories) with an Arthrogen-CIA™ 5-Clone Cocktail Kit (Chondrex Inc., Wash.) following the manufacturer's instructions. Mice were i.p. injected with the cocktail of antibodies on day 0. Three days later, mice were i.p. injected with LPS from *Escherichia coli* 0111:B4 (Chondrex) to trigger arthritis development. Animals were evaluated every 2 days for arthritis incidence. Paw thickness was measured and evaluated individually on a scale of 0-4, where a score of 4 indicates the most severe inflammation. On days 1, 3, 5, and 7, mice were i.v. injected with AS-TNF-α siRNA-SLNs (TNF-α siRNA, 2 mg/kg), AS-SLNs containing a control siRNA (AS-Cont siRNA-SLNs), or left untreated. As a control, one group of healthy mice did not receive any treatment. Mice were euthanized on day 9. The control siRNA in these experiments was Stealth RNAi Negative Control Medium GC Duplex siRNA (Invitrogen), though any siRNA having no substantial effect on either cells or mice (e.g., no known therapeutic effect) can be used.

Micro-CT analysis. The lower feet of CAIA mice were assessed at The University of Texas-Austin High-Resolution X-ray CT Facility. After the mice were euthanized, their lower right feet were immediately collected and stored at −80° C. The specimens were placed with the implant axis perpendicular to the scanning section, and cross-section images of the specimens were acquired at an isotropic resolution of 14.5 μm using a micro-CT system (NSI scanner, Fein Focus High Power Xradia microXCT 400 (Carl Zeiss, Oberkochen, Germany)). Scanning parameters were: voltage of 100 kV, a current of 200 μA, no filter, Perkin Elmer detector, 0.25 pF gain, 1 fps, 1×1 binning, no flip, source to object 155.0 mm, source to detector 1316.961 mm, continuous CT scan, no frames averaged, 0 skip frames, 1800 projections, 5 gain calibrations, 5 mm calibration phantom, data range [−3.0, 40.0] (grayscale adjusted from NSI defaults), hardening correction=0.1. Voxel size=14.5 μm. Total slices=1790. About 30 slides were used to measure calcaneus bone density measured using ImageJ by NIH (Bethesda, Md.).

Histopathologic examination. The lower feet of CAIA mice were immediately fixed in 10% neutral buffered formalin and transferred to 70% ethanol 24 h later. After decalcification, paraffin embedding, and sectioning, the specimens were stained with hematoxylin and eosin (H&E) or safranin O/fast green. H&E slides were given scores of 0-5 for inflammation according to the following criteria: 0, normal; 1, minimal infiltration of inflammatory cells in the periarticular area; 2, mild infiltration; 3, moderate infiltration; 4, marked infiltration; and 5, severe infiltration.

For the safranin O/fast green slides the following criteria was used: 0, normal; 1, minimal-to-mild loss of toluidine blue staining with no obvious chondrocyte loss or collagen disruption; 2, mild loss of toluidine blue staining with focal mild (superficial) chondrocyte loss and/or collagen disruption; 3, moderate loss of toluidine blue staining with multifocal moderate (to middle-zone depth) chondrocyte loss and/or collagen disruption; 4, marked loss of toluidine blue staining with multifocal marked (to deep-zone depth) chondrocyte loss and/or collagen disruption; and 5, severe diffuse loss of toluidine blue staining with multifocal severe (to tidemark depth) chondrocyte loss and/or collagen disruption. Each slide was scored by two independent observers and the average score was used.

Statistical analysis. Statistical analyses were completed by performing analysis of variance followed by Fisher's protected least significant difference procedure. A p value of ≤0.05 (two-tail) was considered significant.

Results and Discussion

Figure 1B:
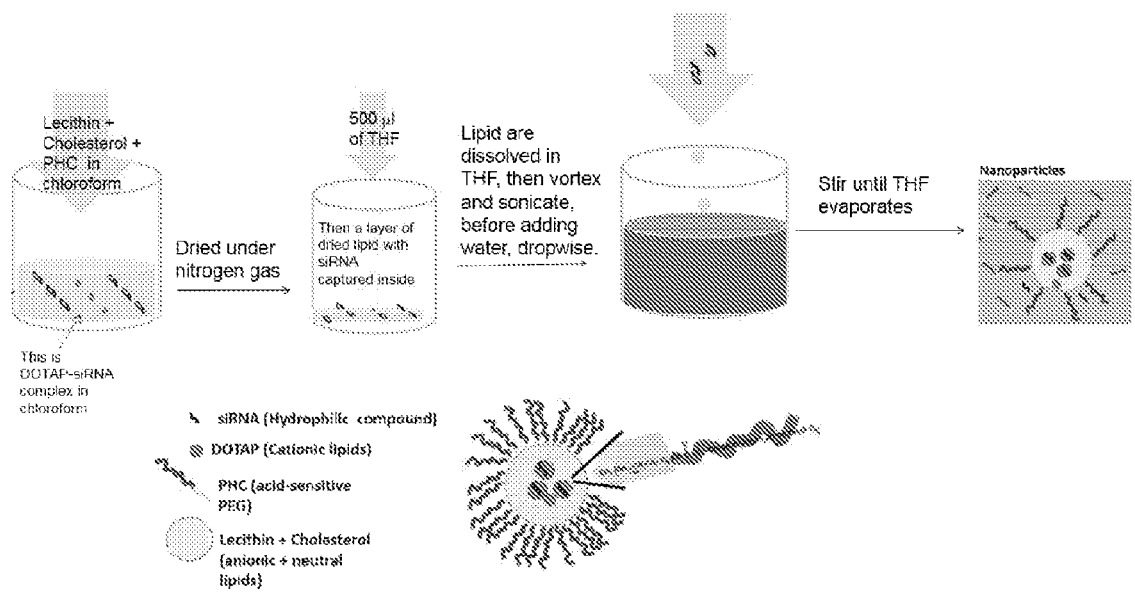

Preparation and in vitro characterization of AS-TNF-α siRNA-SLNs. AS-TNF-α siRNA-SLNs were prepared by encapsulating siRNA complexed with DOTAP into solid lipid nanoparticles comprised of cholesterol, lecithin, and an acid-sensitive stearoyl PEG conjugate (PHC) (FIGS. 1A and 1B). As a control, DOTAP-complexed siRNA was also encapsulated into solid lipid nanoparticles comprised of cholesterol, lecithin, and an acid-insensitive stearoyl PEG conjugate (PAC). The AS-TNF-α siRNA-SLNs had a diameter of about 118±7 nm, with a polydispersity index of 0.16±0.01, and have a zeta potential value of about −13.8±5.8 mV. The distribution of diameters of AS-TNF-α siRNA-SLNs have a mean size of 50 to 180 nm in some experiments. The AS-TNF-α siRNA-SLNs are neutral/slightly negatively surface-charged nanoparticles are preferred to reduce particle aggregation and recognition by the mononuclear phagocyte system (MPS) after i.v. injection, thereby reducing the potential toxicity of nanoparticles. Importantly, the encapsulation efficient (EE) of the siRNA in the nanoparticles was 93±2%. The hydrophobic ion pairing (HIP) technique helps to increase the encapsulation efficiency of the siRNA via complexation with the cationic DOTAP lipid as well as to ensure the incorporation of the siRNA in the lipid core of the SLNs. Transmission electron microscopy images show that the AS-TNF-α siRNA-SLNs are oval to spherical shaped (FIG. 2A). Unlike other siRNA nanoparticles formulations that releases ~20% of siRNA within two days, the data from an in vitro siRNA release study showed that there was minimum burst release of siRNA from the AS-TNF-α siRNA-SLNs; only about 5% of siRNA in a one-month release study (FIG. 2B). The United States Food and Drug Administration (FDA) Nanotechnology Task Force (NTF) recommends no or minimum burst release of the drug from nanoparticles during in vitro evaluation.

Even though another method has been used to prepare solid lipid nanoparticles by wrapping a hydrophobic core with lecithin and amphiphilic PEG conjugates, the nanoparticles reported herein were made by a simpler method and have more favorable in vitro parameters (i.e., minimum burst release of siRNA). It is more likely that the herein disclosed method of preparation, the composition of the SLNs (i.e., addition of cholesterol), and the siRNA to lipid ratio all have contributed to the resultant stable siRNA-nanoparticles with slow siRNA release. Moreover, unlike other methods reported to increase siRNA encapsulation in nanoparticles, the methods used herein do not require change in temperature or any chemical modifications, e.g. TNF-α siRNA thiolation with chitosan and other polymers.

Figure 3A:
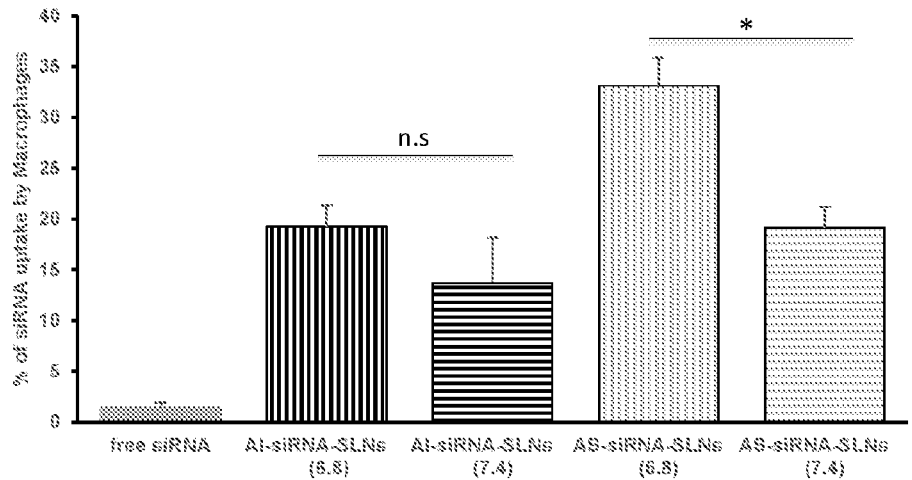
FIGS. 3A and 3B are graphs demonstrating confirmation of acid-sensitivity sheddable PEGylation and the functionality of the AS-TNF-α siRNA-SLNs.

Confirmation of acid-sensitive PEGylation of the AS-TNF-α siRNA-SLNs and their functionality in cell culture. To confirm the acid-sensitive PEGylation of the AS-TNF-α siRNA-SLNs, fluorescein-labeled siRNA was used to prepare AS-siRNA-SLNs (acid-sensitive) and AI-siRNA-SLNs (acid-insensitive; control). Preincubation of the AS-siRNA-SLNs in pH 6.8 PBS (10 mM) for 6 hrs to facilitate the shedding of PEG, as compared to in pH 7.4 PBS (10 mM), before incubating them with J774A.1 cells significantly increased the amount of siRNA associated with the J774A.1 cells (FIG. 3A). For the AI-siRNA-SLNs, preincubation of them in pH 6.8 PBS did not significant increase the amount of siRNA associated with J774A.1 cells (FIG. 3A), indicating that the AS-siRNA-SLNs and the AI-siRNA-SLNs were PEGylated as intended.

Figure 3B:
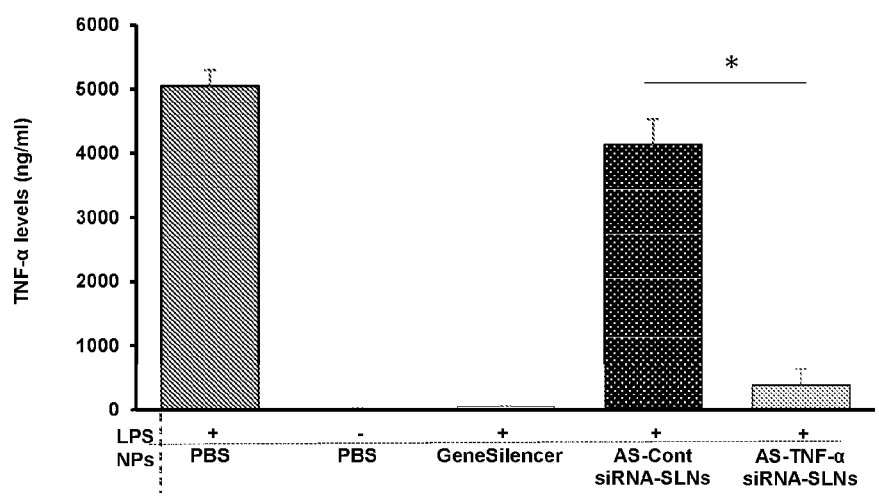

To validate the functionality of the TNF-α siRNA in the AS-TNF-α-siRNA-SLNs, AS-TNF-α-siRNA-SLNs were used to treat LPS-stimulated J774A.1 cells. As controls, LPS-stimulated J774A.1 cells were treated with sterile PBS, siRNA-free AS-SLNs, or AS-siRNA-SLNs containing a control siRNA. As shown in FIG. 3B, only the AS-TNF-α-siRNA-SLNs significantly decreased TNF-α release by LPS-stimulated J774A.1 cells, demonstrating that the siRNA in the AS-TNF-α-siRNA-SLNs was functional.

Figure 4A:
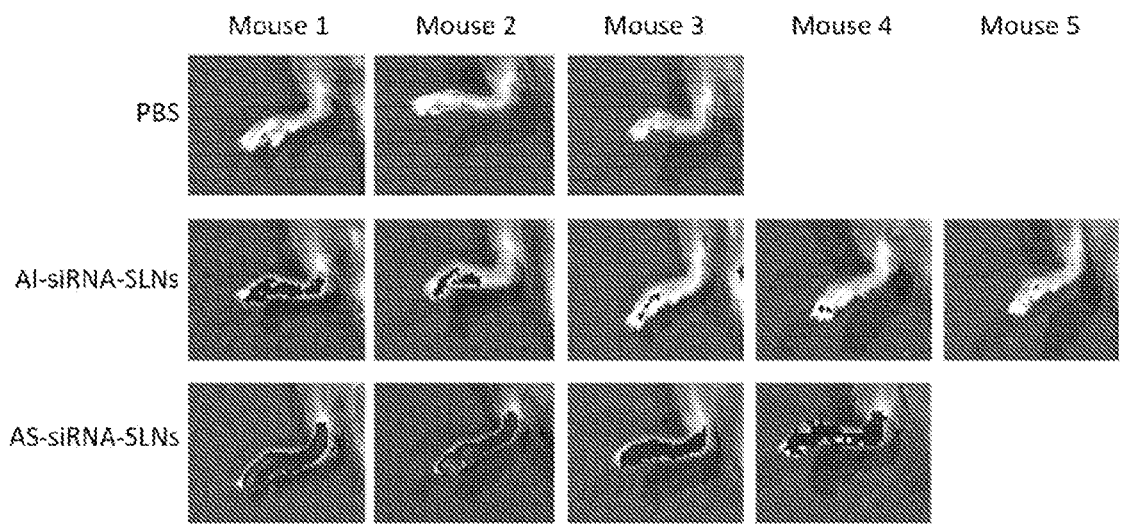
FIGS. 4A-4C show the biodistribution of AI-siRNA-SLNs and AS-siRNA-SLNs in the inflamed foot of mice with LPS-induced chronic inflammation.
Figure 4B:
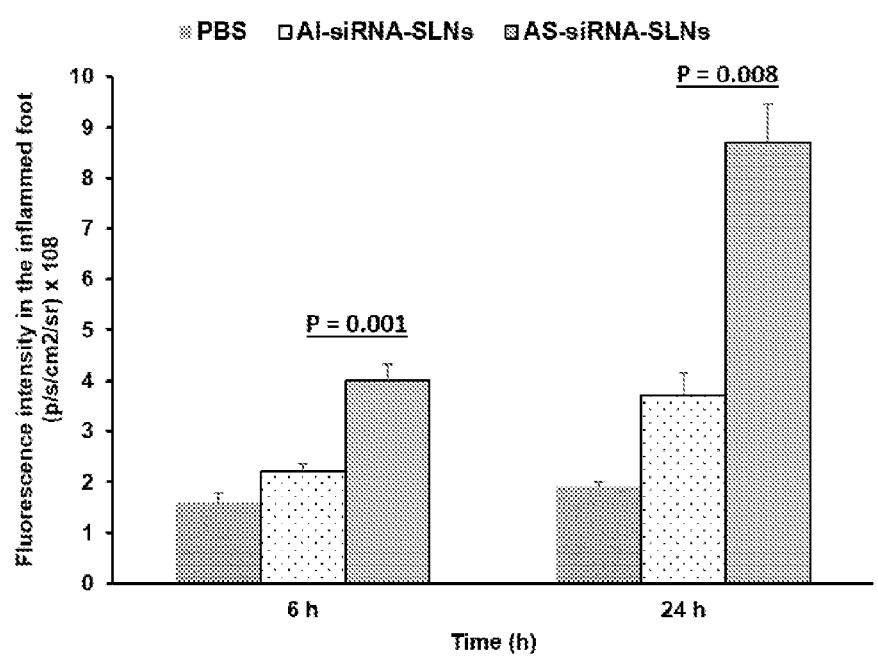
Figure 4C:
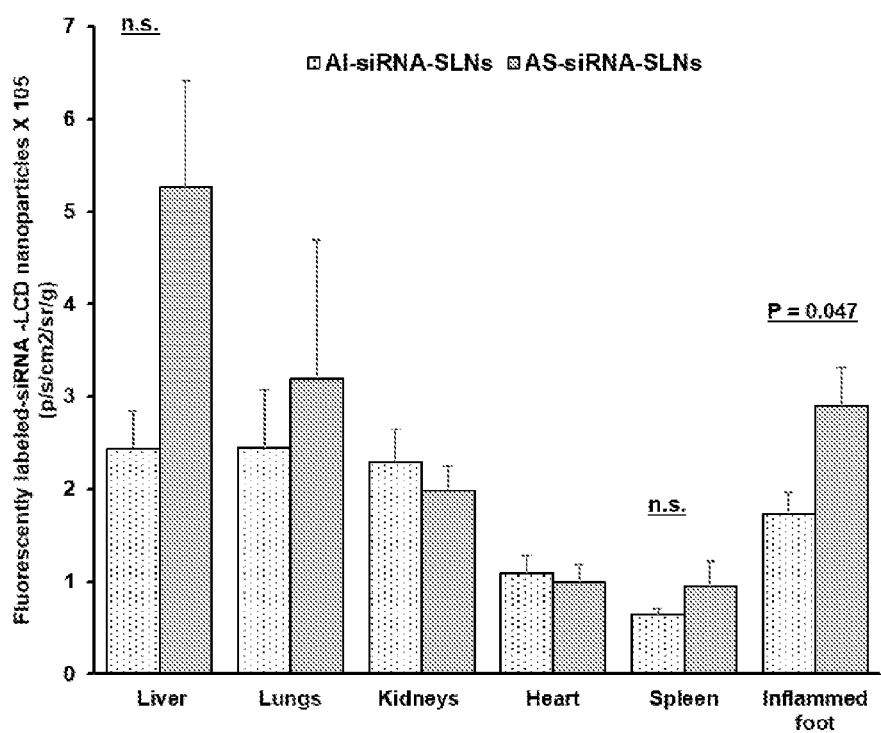

Distribution and accumulation of AS-TNF-α siRNA-SLNs in chronic inflammation sites. Surface modification of nanoparticles with PHC generates a hydrophilic and flexible ring to shield nanoparticles, thereby preventing opsonization and reducing the clearance of nanoparticles by the MPS. The effects of acid-sensitive sheddable PEGylation on the distribution and accumulation of the siRNA-nanoparticles were evaluated in chronic inflammation sites. To that end, accumulation and biodistribution of the AI-siRNA-SLNs and AS-siRNA-SLNs, both fluorescently labeled with TopFluor-cholesterol, in the inflamed feet in mice with LPS-induced chronic inflammation were evaluated. After i.v. injection, the fluorescence intensity in the inflamed foot was measured using an in vivo imaging system 6 and 24 hrs later. As shown in FIGS. 4A and 4B, fluorescence intensity was significantly higher in the inflamed feet in mice i.v. injected with the AS-siRNA-SLNs than in mice injected with the AI-siRNA-SLNs. Ex vivo IVIS™ imaging also showed that biodistribution of the AI-siRNA-SLNs and AS-siRNA-SLNs in major organs of the mice are not significantly different, except in the inflamed feet (FIG. 4C). The extravasation through leaky vasculature and subsequent inflammatory cell-mediated sequestration (i.e., ELVIS) phenomenon in inflamed tissues is likely related to the enhanced accumulation and retention of the AS-siRNA-SLNs, as compared to the AI-siRNA-SLNs. Once the nanoparticles extravasate into inflamed tissues, the low pH environment facilitates the shedding of the PEG chains on the surface of the AS-siRNA-SLNs, thereby facilitating inflammatory cells such as macrophages in the inflamed tissues to readily take up the PEG-shed siRNA-SLNs. However, while AI-siRNA-SLNs can extravasate into inflamed tissues, the retained acid-insensitive PEG chains reduce their uptake by macrophages in inflamed tissues.

Figure 5A:
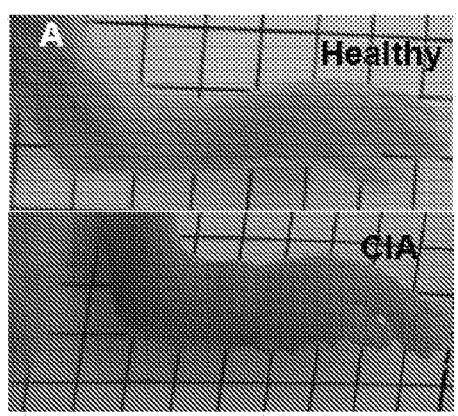
FIGS. 5A-5D show the distribution of siRNA, free or in AS-siRNA-SLNs, in the inflamed feet in CIA mice.
Figure 5B:
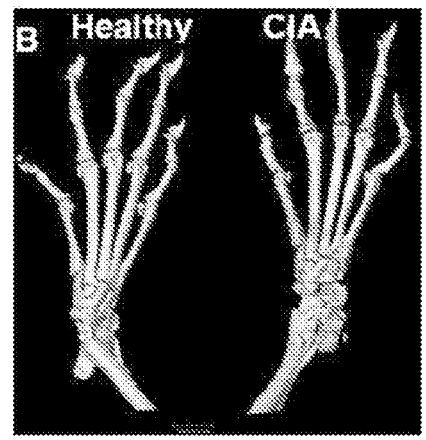
Figure 5C:
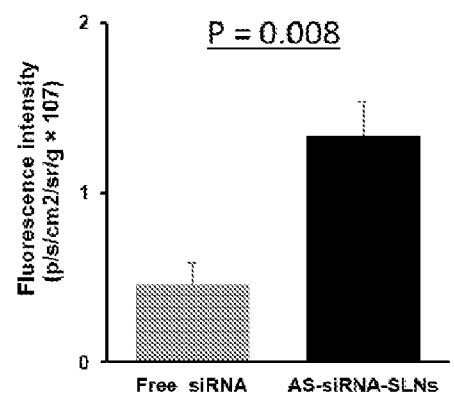
Figure 5D:
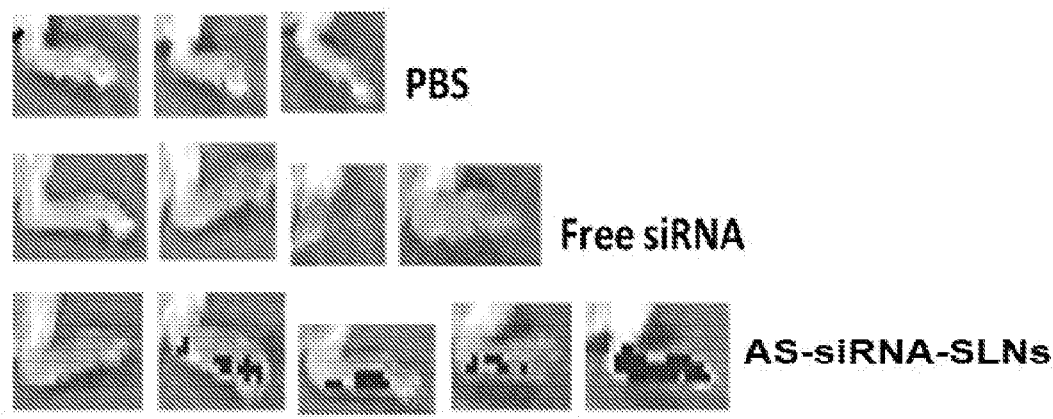

To directly evaluate the extent to which AS-TNF-α-siRNA-SLNs can improve the delivery of TNF-α siRNA into chronic inflammation sites, CIA mice (FIGS. 5A and 5B) were i.v. injected with fluorescently-labeled siRNA, either as free siRNA or in AS-siRNA-SLNs, and fluorescence intensity in the inflamed joints/feet of the mice was measured 48 hrs later. As shown in FIGS. 5C and 5D, the fluorescent signals in the inflamed joints/feet in mice i.v. injected with the AS-siRNA-SLNs were significantly higher than that in mice i.v. injected with free siRNA. This is likely because free siRNA is extensively degraded and cleared through the kidneys. Taken together, data in the LPS-induced chronic inflammation model and the CIA model together clearly demonstrated that acid-sensitive PEGylated AS-siRNA-SLNs significantly increased the distribution and retention of siRNAs in chronic inflammation sites in mouse models.

Figure 6A:
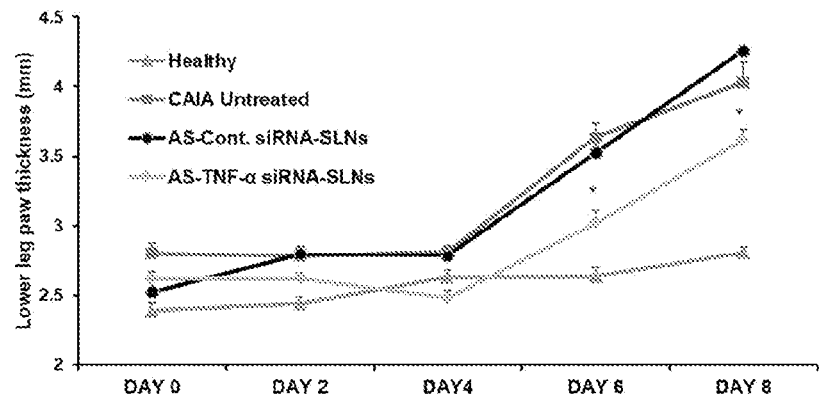
FIGS. 6A-6G show the effects of AS-TNF-a siRNA-SLNs in a mouse model of CAIA.
Figure 6B:
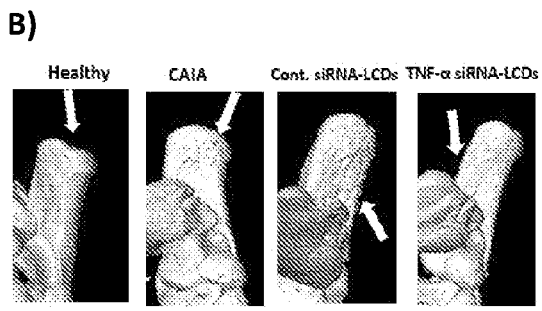
Figure 6C:
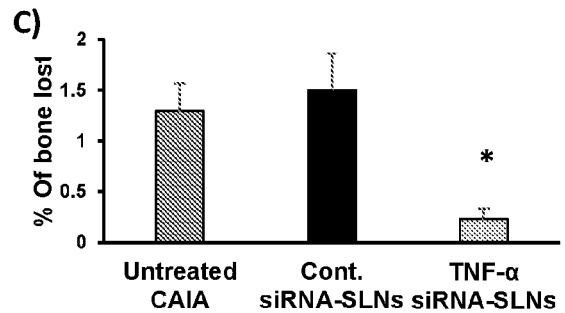

Therapeutic effect of AS-TNF-α siRNA-SLNs in mice with CAIA. The therapeutic efficacy of AS-TNF-α-siRNA-SLNs was evaluated in a mouse model of CAIA. CAIA model was established by injecting mice intraperitoneally with Arthrogen-CIA™ 5-Clone Cocktail Kit. The CAIA model has several advantages over the CIA model such as rapid disease onset, higher disease rate and wider spectrum of strains to choose from. Mice were then i.v. injected with AS-TNF-α-siRNA-SLNs on days 1, 3, 5 and 7. Control mice were left untreated or i.v. injected with AS-siRNA-SLNs containing control siRNA. As shown in FIG. 6A, the thickness of untreated mouse paws increased continuously. Treatment with AS-siRNA-SLNs prepared with control siRNA did not significantly affect the thickness of the mouse paws, as compared to untreated. However, treatment with AS-TNF-α-siRNA-SLNs significantly reduced paw thickness on days 6 and 8 (FIG. 6A). Clinical scores on day 6 also showed a significant reduction in inflammation in mice treated with AS-TNF-α-siRNA-SLNs. Moreover, micro-CT 3D images of the calcaneus bone of mice shows less roughness in mice treated with AS-TNF-α-siRNA-SLNs than in mice treated with nanoparticles prepared with a control siRNA (AS-Cont siRNA-SLN) (FIG. 6B). CAIA also caused bone loss (FIG. 6C). Treatment with AS-TNF-α-siRNA-SLNs, but not with AS-Cont siRNA-SLNs, significantly inhibited bone loss (FIG. 6C).

Figure 6D:
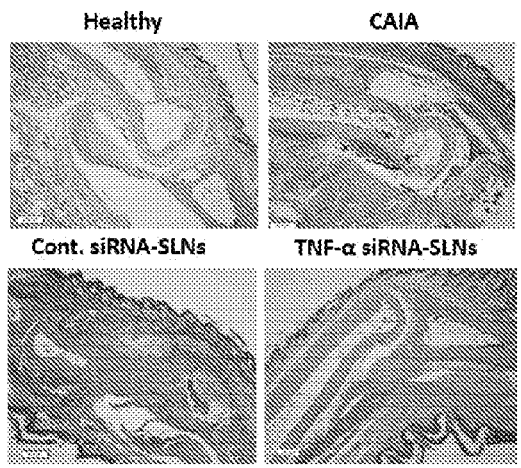
Figure 6E:
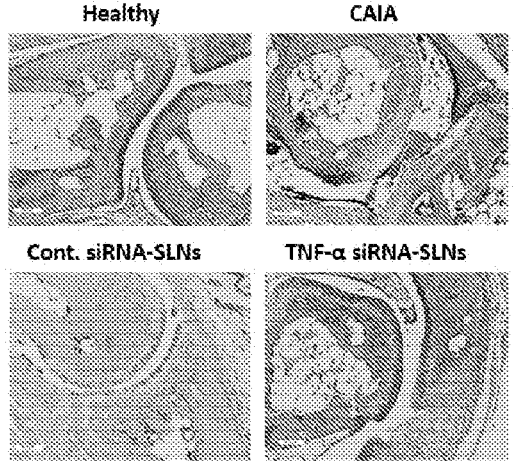
Figure 6F:
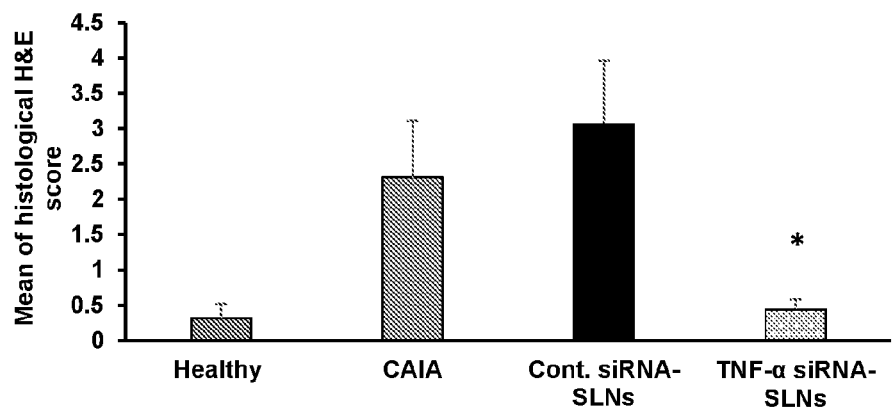
Figure 6G:
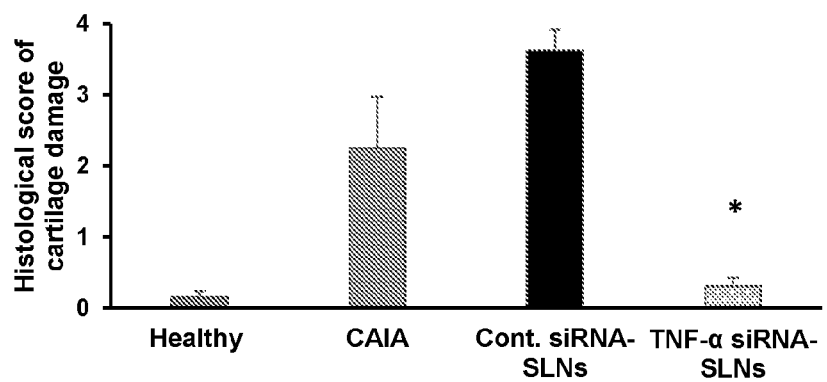
Figure 7:
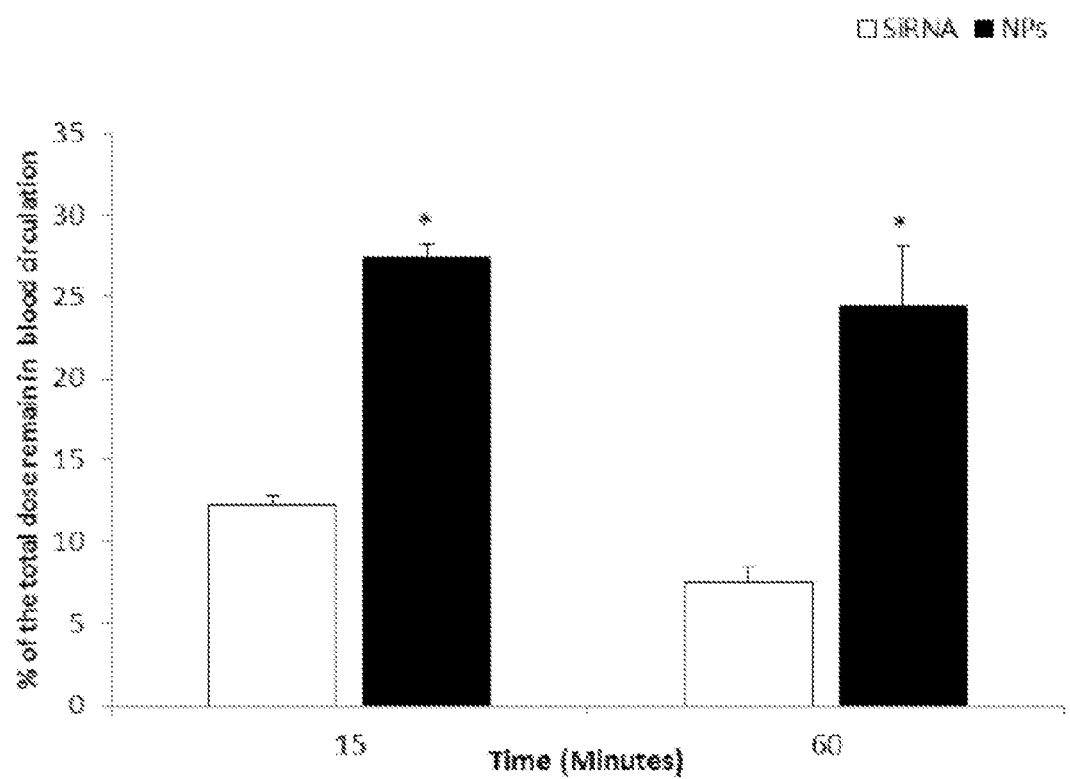
FIG. 7 shows AS-siRNA-LCD increased the circulation time of siRNA compared to naked siRNA. White mice were separated into three groups and treated with either PBS control, free siRNA ("siRNA") or AS-siRNA-LCD ("NPs"). 10 μL of blood from each mouse were diluted in 100 μL PBS, measurements were taken using a plate reader, and results were normalized to PBS-treated mice. Data show that the clearance rate within 45 minutes is about 40 percent for siRNA and 10 percent for AS-siRNA-LCD nanoparticles. Thus, the half-life of free siRNA is significantly lower than AS-siRNA-LCD nanoparticles.
Figure 8:
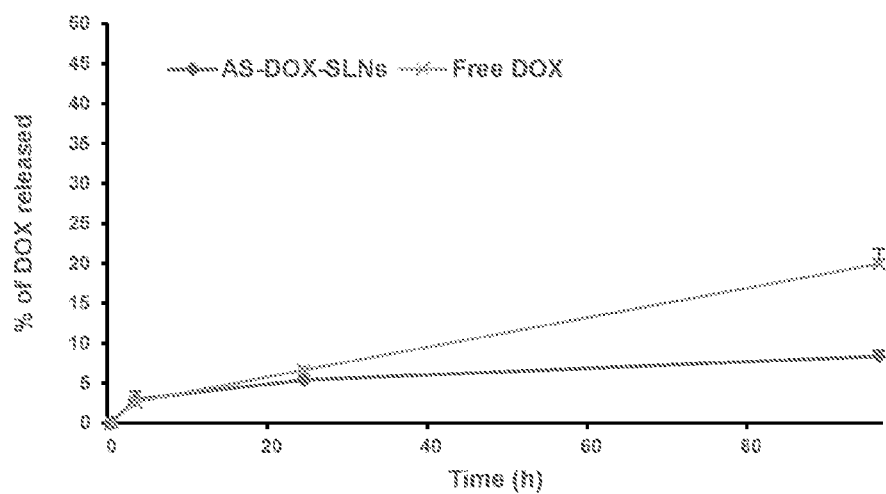
FIG. 8 shows the burst release characteristics of AS-DOX-SLN nanoparticles. A minimum burst release of DOX (<5%) occurred from AS-DOX-SLNs nanoparticles, as measured by fluorescence intensity using a BioTek Synergy HT Multi-Mode Microplate Reader. Data are mean±S.D. (n=3). The diffusion of free DOX across the membrane was also determined to make sure it was not rate-limiting.
Figure 9:
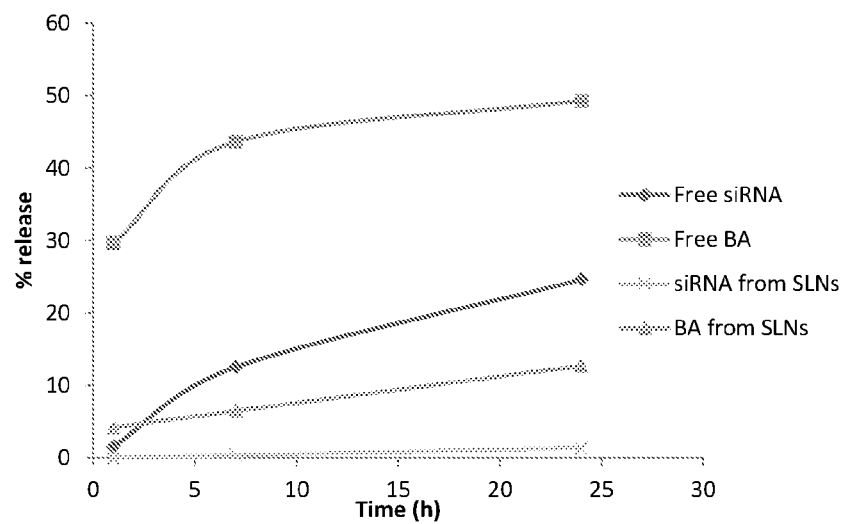
FIG. 9 is a graph showing in the vitro release profiles of betamethasone acetate (BA) and siRNA from the BA-incorporated siRNA-SLNs. A small amount of BA is released as a burst prior to 1 h, but the overall release is about 10% in 24 h. siRNA release is less than 2% at 24 h. Data are mean of three samples. As controls, the diffusion profiles of the siRNA and BA across the dialysis membrane (MWCO, 50 kDa) are also included.

Shown in FIGS. 6D and 6E are mouse hind leg joints after H&E and safranin-O staining, respectively. CAIA caused inflammatory cell infiltration in the joints and damages to articular cartilage and bones (FIGS. 6D and 6E). Treatment with AS-Cont siRNA-SLNs did not show any significant effect. However, CAIA mice treated with AS-TNF-α-siRNA-SLNs showed only minimum inflammatory cell infiltration in the joints, with intact articular cartilage and healthy bones (FIGS. 6D and 6E). Histopathological evaluation also showed that mice treated with AS-TNF-α-siRNA-SLNs had significantly lower H&E and cartilage damage scores than untreated mice or mice treated with AS-Cont siRNA-SLNs. The observed clinical findings in the AS-TNF-α-siRNA-SLNs is likely due to their silencing of TNF-α production by macrophages in the inflamed joints, although TNF-α was not detected in the inflamed tissue or the serum samples of any of the mice. In another study, concentration of TNF-α in hind paws was lower than the detection limit of ELISA. It is important to mention that during the study, there was not any significant change in mouse body weight between all the CAIA treated groups. An i.v. injection of naked nucleic acid including siRNAs can induce a strong innate immune response triggered by the systemic induction of proinflammatory cytokines such as type I interferons. No significant differences were detected in the serum IL-6 levels between AS-TNF-α siRNA-SLNs treated mice and untreated mice. The elimination of burst released TNF-α siRNA from the AS-TNF-α siRNA-SLNs likely helped to avoid or minimize the immunostimulatory activity of TNF-α siRNA in circulation.

TNF-α siRNA nanoparticle formulations showed promising effects against arthritis in a mouse model of CAIA. The nanoparticles have high siRNA encapsulation efficiency (>90%) and minimum burst release (<5%). The nanoparticles also increase the delivery of the siRNA into chronic inflammation sites.

REFERENCES

1. Jahoor, A., Patel, R., Bryan, A., Do, C., Krier, J., Watters, C., Wahli, W., Li, G., Williams, S. C. and Rumbaugh, K. P. (2008) Peroxisome proliferator-activated receptors mediate host cell proinflammatory responses to *Pseudomonas aeruginosa* autoinducer. J Bacteriol, 190, 4408-4415.

2. Choy, E. H. and Panayi, G. S. (2001) Cytokine pathways and joint inflammation in rheumatoid arthritis. N Engl J Med, 344, 907-916.

3. van de Putte, L. B., Rau, R., Breedveld, F. C., Kalden, J. R., Malaise, M. G., van Riel, P. L., Schattenkirchner, M., Emery, P., Burmester, G. R., Zeidler, H. et al. (2003) Efficacy and safety of the fully human anti-tumour necrosis factor alpha monoclonal antibody adalimumab (D2E7) in DMARD refractory patients with rheumatoid arthritis: a 12 week, phase II study. Ann Rheum Dis, 62, 1168-1177.

4. Schiff, M. H., Burmester, G. R., Kent, J. D., Pangan, A. L., Kupper, H., Fitzpatrick, S. B. and Donovan, C. (2006) Safety analyses of adalimumab (HUMIRA) in global clinical trials and US postmarketing surveillance of patients with rheumatoid arthritis. Ann Rheum Dis, 65, 889-894.

5. Schreiber, S. (2011) Certolizumab pegol for the treatment of Crohn's disease. Therap Adv Gastroenterol, 4, 375-389.

6. D'Haens, G. R. (1999) Infliximab (Remicade), a new biological treatment for Crohn's disease. Ital J Gastroenterol Hepatol, 31, 519-520.

7. Weinblatt, M. E., Bingham, C. O., 3rd, Mendelsohn, A. M., Kim, L., Mack, M., Lu, J., Baker, D. and Westhovens, R. (2013) Intravenous golimumab is effective in patients with active rheumatoid arthritis despite methotrexate therapy with responses as early as week 2: results of the phase 3, randomised, multicentre, double-blind, placebo-controlled GO-FURTHER trial. Ann Rheum Dis, 72, 381-389.

12. Gao, S., Dagnaes-Hansen, F., Nielsen, E. J. B., Wengel, J., Besenbacher, F., Howard, K. A. and Kjems, J. (2009) The Effect of Chemical Modification and Nanoparticle Formulation on Stability and Biodistribution of siRNA in Mice. Mol Ther, 17, 1225-1233.

13. Leng, Q., Woodle, M. C., Lu, P. Y. and Mixson, A. J. (2009) ADVANCES IN SYSTEMIC siRNA DELIVERY. Drug Future, 34, 721-737.

14. Howard, K. A., Paludan, S. R., Behlke, M. A., Besenbacher, F., Deleuran, B. and Kjems, J. (2009) Chitosan/siRNA nanoparticle-mediated TNF-alpha knockdown in peritoneal macrophages for anti-inflammatory treatment in a murine arthritis model. Mol Ther, 17, 162-168.

15. Kim, S S , Ye, C., Kumar, P., Chiu, I., Subramanya, S., Wu, H., Shankar, P. and Manjunath, N. (2010) Targeted delivery of siRNA to macrophages for anti-inflammatory treatment. Mol Ther, 18, 993-1001.

16. Komano, Y., Yagi, N., Onoue, I., Kaneko, K., Miyasaka, N. and Nanki, T. (2012) Arthritic joint-targeting small interfering RNA-encapsulated liposome: implication for treatment strategy for rheumatoid arthritis. J Pharmacol Exp Ther, 340, 109-113.

17. Presumey, J., Salzano, G., Courties, G., Shires, M., Ponchel, F., Jorgensen, C., Apparailly, F. and De Rosa, G. (2012) PLGA microspheres encapsulating siRNA anti-TNFalpha: efficient RNAi-mediated treatment of arthritic joints. Eur J Pharm Biopharm, 82, 457-464.

18. to Boekhorst, B. C., Jensen, L. B., Colombo, S., Varkouhi, A. K., Schiffelers, R. M., Lammers, T., Storm, G., Nielsen, H. M., Strijkers, G. J., Foged, C. et al. (2012) MRI-assessed therapeutic effects of locally administered PLGA nanoparticles loaded with anti-inflammatory siRNA in a murine arthritis model. J Control Release, 161, 772-780.

19. Lee, S. J., Lee, A., Hwang, S. R., Park, J. S., Jang, J., Huh, M. S., Jo, D. G., Yoon, S. Y., Byun, Y., Kim, S. H. et al. (2014) TNF-alpha gene silencing using polymerized siRNA/thiolated glycol chitosan nanoparticles for rheumatoid arthritis. Mol Ther, 22, 397-408.

20. Lobovkina, T., Jacobson, G. B., Gonzalez-Gonzalez, E., Hickerson, R. P., Leake, D., Kaspar, R. L., Contag, C. H. and Zare, R. N. (2011) In vivo sustained release of siRNA from solid lipid nanoparticles. ACS Nano, 5, 9977-9983.

21. Choi, B., Cui, Z. K., Kim, S., Fan, J., Wu, B. M. and Lee, M. (2015) Glutamine-chitosan modified calcium phosphate nanoparticles for efficient siRNA delivery and osteogenic differentiation. J Mater Chem B Mater Biol Med, 3, 6448-6455.

22. Zhou, Z., Li, H., Wang, K., Guo, Q., Li, C., Jiang, H., Hu, Y., Oupicky, D. and Sun, M. (2017) Bioreducible Cross-Linked Hyaluronic Acid/Calcium Phosphate Hybrid Nanoparticles for Specific Delivery of siRNA in Melanoma Tumor Therapy. ACS Appl Mater Interfaces, 9, 14576-14589.

23. Cun, D. M., Jensen, D. K., Maltesen, M. J., Bunker, M., Whiteside, P., Scurr, D., Foged, C. and Nielsen, H. M. (2011) High loading efficiency and sustained release of siRNA encapsulated in PLGA nanoparticles: Quality by design optimization and characterization. European Journal of Pharmaceutics and Biopharmaceutics, 77, 26-35.

24. Wang, J., Lu, Z., Wientjes, M. G. and Au, J. L. (2010) Delivery of siRNA therapeutics: barriers and carriers. AAPS J, 12, 492-503.

25. Zhu, S. J., Wonganan, P., Lansakara-P, D. S. P., O'Mary, H. L., Li, Y. and Cui, Z. R. (2013) The effect of the acid-sensitivity of 4-(N)-stearoyl gemcitabine-loaded micelles on drug resistance caused by RRM1 overexpression. Biomaterials, 34, 2327-2339.

26. Tseng, J. C. and Kung, A. L. (2013) In vivo imaging method to distinguish acute and chronic inflammation. J Vis Exp, 78, 50690.

27. Lu, L. D., Stump, K. L. and Seavey, M. M. (2010) Novel method of monitoring trace cytokines and activated STAT molecules in the paws of arthritic mice using multiplex bead technology. BMC Immunol, 11, 55.

28. Chia, W. T., Chen, Y. W., Cheng, L. Y., Lee, H. S., Chang, D. M. and Sytwu, H. K. (2008) MMP-9 mRNA as a therapeutic marker in acute and chronic stages of arthritis induced by type II collagen antibody. J Formos Med Assoc, 107, 245-252.

29. Bendele, A. M., Chlipala, E. S., Scherrer, J., Frazier, J., Sennello, G., Rich, W. J. and Edwards, C. K., 3rd. (2000) Combination benefit of treatment with the cytokine inhibitors interleukin-1 receptor antagonist and PEGylated soluble tumor necrosis factor receptor type I in animal models of rheumatoid arthritis. Arthritis Rheum, 43, 2648-2659.

30. Ye, C., Bhan, A. K., Deshpande, V., Shankar, P. and Manjunath, N. (2013) Silencing TNF-alpha in macrophages and dendritic cells for arthritis treatment. Scand J Rheumatol, 42, 266-269.

32. (2006) Internal nanotechnology task force for USFDA. Nanomedicine-Uk, 1, 264-264.

33. Aldayel, A. M., Naguib, Y. W., O/'Mary, H. L., Li, X., Niu, M., Ruwona, T. B. and Cui, Z. (2016) Acid-Sensitive Sheddable PEGylated PLGA Nanoparticles Increase the Delivery of TNF-[alpha] siRNA in Chronic Inflammation Sites. Mol Ther Nucleic Acids, 5, e340.

34. Khachigian, L. M. (2006) Collagen antibody-induced arthritis. Nat Protoc, 1, 2512-2516.

35. Kanasty, R. L., Whitehead, K. A., Vegas, A. J. and Anderson, D. G. (2012) Action and reaction: the biological response to siRNA and its delivery vehicles. Mol Ther, 20, 513-524.

36. Jackson, A. L. and Linsley, P. S. (2010) Recognizing and avoiding siRNA off-target effects for target identification and therapeutic application. Nat Rev Drug Discov, 9, 57-67.

Example 2

Incorporation of Doxorubicin into Acid-Sensitive Sheddable PEGylated Solid Lipid Nanoparticles Hydrophobic, water-insoluble molecules are readily incorporated into the solid lipid nanoparticles. However, solid lipid nanoparticles were also prepared to encapsulate or incorporate small water-soluble molecules (e.g. doxorubicin, DOX). The preparation process involves three organic solvents and one aqueous solvent, wherein one of the organic solvents is water immiscible (e.g. chloroform, dichloromethane (DCM)), and another organic solvent is water miscible (e.g. tetrahydrofuran (THF), ethanol, methanol). The preparation process involves a lipid, such as DOTAP, in a water immiscible organic solvent, such as chloroform, at a concentration of 2-4 mg/ml, and adding this solution slowly to DOX in water solution while stirring. After sonication and vortexing, methanol is added to the mixture at a ratio of methanol to chloroform of 2:1 (v/v). The mixture is then stirred at room temperature for 15-30 min to allow the lipid and DOX to form complexes. Additional chloroform is then added to the mixture to create two immiscible layers, water phase on the top and chloroform phase on the bottom. The top layer is discarded. The bottom layer contains the DOX-lipid complexes. Another mix of lipids with, for example lecithin and cholesterol at a 2:1 ratio (w/w) (1.6 mg and 3.2 mg, respectively, dissolved in chloroform), is added to the DOX-DOTAP complexes while stirring. In addition, an amphiphilic molecule, such as stearoyl-PEG2000 conjugate may be dissolved in chloroform and added to the solution as well. After 5-10 min of stirring, the formulation is dried using, for example, nitrogen gas. After the water immiscible solvent, e.g. chloroform, is evaporated, the remainder is hydrated in another organic solvent that is miscible with water such as THF, vortexed and sonicated, and then added drop-wise to an aqueous phase such as water while stirring. Solid lipid nanoparticles are formed after the organic solvent is evaporated.

Characterization of nanoparticles. The particle size, polydispersity index (PDI), and zeta potential of the nanoparticles were determined using a Malvern Zeta Sizer Nano ZS (Westborough, Mass.). To determine the encapsulation/incorporation efficiency of DOX in the nanoparticles, nanoparticles were centrifuged to measure the florescent intensity of unencapsulated DOX in water phase. The fluorescence intensity was measured using a BioTek Synergy HT Multi-Mode Microplate Reader (Winooski, Vt., Ex=485 nm, Em=528 nm). Results are shown in Table 1:

TABLE 1

| Characterization of DOX-SLNs. | | | |
| --- | --- | --- | --- |
| Particles size (nm) | PDI | Zeta potential (mV) | Encapsulation efficiency |
| 77 ± 3 | 0.27 ± 0.03 | 25.03 ± 0.07 | 85 ± 0.5% |

Figures 10A, 10B:
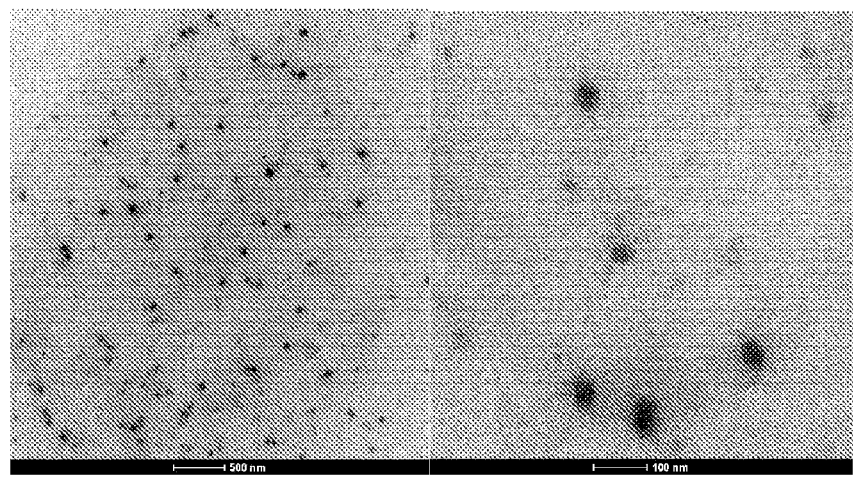
FIGS. 10A and 10B are images depicting the physical characterization of AS-MTX-siRNA-DOTAP-SLNs.

In vitro release of DOX from nanoparticles. About 9 mg of the DOX-incorporated SLNs were suspended in 1 ml PBS (10 mM, pH 7.4) inside a dialysis bag (MWCO 50 kDa, Spectrum Laboratories, Calif.), which was then placed into 50 ml PBS (10 mM, pH 7.4) and maintained in a shaker incubator (MAQ 5000, MODEL 4350, Thermo Fisher Scientific, Waltham, Mass.) (100 rpm, 37° C.). At given time points (3, 24, 96 hrs), the amount of DOX in the release medium was measured by detecting fluorescence intensity using a BioTek Synergy HT Multi-Mode Microplate Reader (FIG. 10). The percent of DOX released was calculated using the following equation: % released=100×fluorescence intensity in the release medium/total fluorescence intensity of the encapsulated DOX.

Example 3

Incorporation of Betamethasone into siRNA-Containing Acid-Sensitive Sheddable PEGylated Solid Lipid Nanoparticles Inclusion of a glucocorticoid (e.g. betamethasone) into the method to develop an anti-inflammatory delivery vehicle was also investigated. Glucocorticoids are hydrophobic and poorly water-soluble molecules, and thus readily incorporated into the solid lipid nanoparticles. Furthermore, glucocorticoids are structurally similar to cholesterol. Thus, incorporation of betamethasone is possible without sacrificing the efficiency of siRNA encapsulation.

Method of preparation. The method to prepare nanoparticles comprising betamethasone involves minimal modification to the base procedure for preparing solid lipid nanoparticles. A cationic lipid (e.g. DOTAP) was dissolved in a water immiscible solvent (e.g. chloroform) at a concentration of approximately 2 to 4 mg/mL. This lipid solution was added dropwise to an aqueous solution of siRNA under stirring and then sonicated for a few minutes, after which time the mixture was stirred for 30 minutes. Methanol was added to the siRNA-lipid mixture at a volume twice that of the water immiscible solvent (e.g. 2:1 methanol to chloroform). The mixture was further stirred at room temperature for 30 minutes to 1 hour to form siRNA-lipid complexes. After complexes formed, additional chloroform was added to the mixture to create two distinct aqueous and organic layers. The aqueous layer was discarded and the siRNA-lipid complexes in the organic layer were retained. Another mixture of lipids (e.g. lecithin and cholesterol) were dissolved in a water immiscible solvent (e.g. chloroform) at a 2:1 (w/w) ratio. In addition, an amphiphilic molecule (e.g. stearoyl-PEG2000 conjugate) and a glucocorticoid (e.g. betamethasone acetate) were dissolved in a water immiscible solvent (e.g. chloroform) and added to the reserved organic layer along with the 2:1 (w/w) lipid mixture under stirring. After stirring for a few minutes, the water immiscible solvent was evaporated using nitrogen gas, and the remaining film was re-dissolved using a water miscible solvent (e.g. THF). Once dissolved, the water miscible solvent was added dropwise to a sufficient volume of aqueous phase. Solid lipid nanoparticles were formed through precipitation as the solvent was evaporated.

Characterization of nanoparticles. The particle size, polydispersity index (PDI), and zeta potential of the nanoparticles were determined using a Malvern Zeta Sizer Nano ZS (Westborough, Mass.). To determine the encapsulation/incorporation efficiency of siRNA and betamethasone, the nanoparticles were collected using an Amicon ultra centrifugal filter device (MilliporeSigma, Billerica, Mass.) and the filtrate was analyzed. The fluorescence intensity of siRNA in the filtrate was measured using a BioTek Synergy HT Multi-Mode Microplate Reader (Winooski, Vt., Ex=485 nm, Em=528 nm), which was then used to indirectly calculate the encapsulation efficiency of siRNA. The efficiency of betamethasone incorporation into the formulation was evaluated using an Agilent 1260 Infinity LC equipped with an Agilent ZORBAX Eclipse PlusC18 column (5 μm, 4.6 mm×150 mm) for chromatographic separation. Filtrate was mixed with an equal volume of methanol and injected into the HPLC system. Measurements were made at 248 nm and 30° C. and a flow rate of 1.5 mL/min. Mobile phase consisted of acetonitrile and water at a ratio of 40:60. The concentration of betamethasone in the filtrate was then used to indirectly calculate the amount of betamethasone contained within the nanoparticles. Results are shown in Table 2:

TABLE 2

Characterization of BA-incorporated siRNA-SLNs.

| Particles size (nm) | PDI | Zeta potential (mV) | Encapsulation efficiency (siRNA) | Encapsulation efficiency (BA) |
|---|---|---|---|---|
| 141.4 ± 1.4 | 0.18 ± 0.01 | 0.03 ± 0.02 | 95.02 ± 0.12% | 76.03 ± 0.66% |

In vitro release of siRNA and betamethasone from the nanoparticles. Briefly, approximately 9.5 mg of BA-incorporated siRNA nanoparticles were suspended in 5 mL PBS (10 mM, pH 7.4) inside a dialysis bag (MWCO 50 kDa, Spectrum Laboratories, Calif.), which was then placed into 35 ml PBS (10 mM, pH 7.4) and maintained in a shaker incubator (MAQ 5000, MODEL 4350, Thermo Fisher Scientific, Waltham, Mass.) (110 rpm, 37° C.). At given time points (1, 7, 24 h), the release media was completely removed and replaced. The release of siRNA was determined by measuring the fluorescence intensity of the collected release media using a BioTek Synergy HT Multi-Mode Microplate Reader. The percent of siRNA released was determined using a standard curve based on the fluorescence intensity of encapsulated siRNA. Fluorescence intensity equivalent to 25%, 50%, 75%, and 100% release was determined using prepared standards. The amount of release was calculated using an equation fit to this standard curve.

To measure the release of betamethasone, a 1 mL aliquot of the release media was spiked with 10 μg of prednisolone as an internal standard and betamethasone was extracted from the release media using an equal volume of ethyl acetate. Ethyl acetate was evaporated using nitrogen gas, after which the remaining betamethasone was dissolved using 1:1 methanol and water. The dissolved samples were then measured using an Agilent 1260 Infinity LC equipped with an Agilent ZORBAX Eclipse PlusC18 column (5 μm, 4.6 mm×150 mm) for chromatographic separation. Filtrate from centrifugation was mixed with an equal volume of methanol and injected into the HPLC system. Measurements were made at 248 nm and 30° C. and a flow rate of 1.5 mL/min. Mobile phase consisted of acetonitrile and water at a ratio of 40:60. The concentration of betamethasone in the release media was calculated and used to determine the percent of total drug released from the formulation.

Example 4

Incorporation of Methotrexate into siRNA-Containing Acid-Sensitive Sheddable PEGylated Solid Lipid Nanoparticles Solid lipid nanoparticles were prepared with incorporated small, poorly water-soluble molecules (e.g. Methotrexate, MTX). MTX is practically insoluble in water, but its solubility is increased in lower pH. At lower pH, the fraction of ionized MTX is increased, and the ionized MTX is positively charged. When MTX in a low pH solution is mixed with siRNA, the MTX and siRNA form complexes that are less soluble.

MTX was measured using HPLC. The morphology of the AS-MTX-siRNA-SLNs were examined using transmission electron microscopy. Results are shown in Table 3. Data are mean±S.D. (n=3):

TABLE 3

Characterization of AS-MTX-siRNA-DOTAP-SLNs.

| Particles size (nm) | PDI | Zeta potential (mV) | Encapsulation efficiency (siRNA) | Encapsulation efficiency (MTX) |
|---|---|---|---|---|
| 108.5 ± 11.0 | 0.28 ± 0.03 | 28.7 ± 1.4 | 72.3 ± 2.2% | 23.4 ± 0.03% |

Method of preparation. The preparation process overall involves three organic solvents and one aqueous solvent, wherein one of the organic solvents is water immiscible (e.g. chloroform, dichloromethane (DCM)), and another organic solvent is water miscible (e.g. tetrahydrofuran (THF), ethanol, methanol). First, 1 mg of MTX was dissolved in 1 ml of 0.1M of hydrochloric-acid. Then 50 μl of the MTX stock solution was mixed with 450 μl of water (in Container A). Then 50 μl of 20 μM of siRNA was added dropwise to Container A while stirring to form complexes. A cationic lipid, such as DOTAP, in a water immiscible organic solvent, such as chloroform, at a concentration of 2-4 mg/ml, was slowly added into the solution containing the MTX-siRNA complexes while stirring (to further increase the lipophilicity of the MTX-siRNA complexes). After sonication and vortexing, methanol was added to the mixture at a ratio of methanol to chloroform of 2:1 (v/v). The mixture was stirred at room temperature for 15-30 min to allow the cationic agents to complex on the MTX-siRNA complexes. Additional chloroform was added to the mixture to create two immiscible layers, water phase on the top, chloroform phase on the bottom. The top layer was discarded. The bottom layer contained the MTX-siRNA-DOTAP complexes. Another mix of lipids with, for example, lecithin and cholesterol at a 2:1 ratio (w/w) (1.6 mg and 3.2 mg, respectively, dissolved in chloroform) was added to the MTX-siRNA-DOTAP complexes while stirring. In addition, an amphiphilic molecule, such as stearoyl-PEG2000 conjugate, was dissolved in chloroform and added to the solution. After 5-10 min of stirring, the formulation was dried using, for example, nitrogen gas. After the water immiscible solvent, e.g. chloroform, was evaporated, the remaining was hydrated in another organic solvent that is miscible with water such as THF, vortexed and sonicated, and then added drop-wise to an aqueous phase such as water while stirring. Solid lipid nanoparticles were formed after the organic solvent was evaporated.

Characterization of nanoparticles. The particle size, polydispersity index (PDI), and zeta potential of the nanoparticles were determined using a Malvern Zeta Sizer Nano ZS (Westborough, Mass.). To determine the encapsulation/incorporation efficiency of siRNA and MTX in the nanoparticles, the nanoparticles were centrifuged to measure the florescent intensity of the unencapsulated siRNA in supernatant. The fluorescence intensity was measured using a BioTek Synergy HT Multi-Mode Microplate Reader (Winooski, Vt., Ex=485 nm, Em=528 nm). The unencapsulated Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A nanoparticle comprising: a lipid core comprising a sterol; and a complex comprising a first and a second therapeutic agent, wherein the first therapeutic agent comprises a polynucleotide and the second therapeutic agent comprises a small molecule; wherein the complex is encapsulated within the lipid core.

2. The nanoparticle of claim 1, wherein the first agent is siRNA.

3. The nanoparticle of claim 1, further comprising an acid-sheddable PEG.

4. The nanoparticle of claim 1, wherein the lipid core further comprises an anionic lipid or a neutral lipid.

5. The nanoparticle of claim 4, wherein the anionic lipid comprises lecithin.

6. The nanoparticle of claim 1, wherein the sterol comprises cholesterol.

7. The nanoparticle of claim 1, wherein the nanoparticle has an overall neutral or anionic charge.

8. The nanoparticle of claim 1, wherein the nanoparticle has a diameter of 300 nm or less.

9. The nanoparticle of claim 1, wherein the complex further comprises a cationic agent.

10. The nanoparticle of claim 9, wherein the cationic agent and therapeutic agent form a complex.

11. The nanoparticle of claim 1, wherein the ratio of therapeutic agent to cationic agent is from 1:28 to 1:1 by weight.

12. The nanoparticle of claim 11, wherein the ratio of therapeutic agent to cationic agent is from 1:27 to 1:26 by weight.

13. The nanoparticle of claim 12, wherein the therapeutic agent comprises siRNA and the cationic agent comprises DOTAP.

14. The nanoparticle of claim 9, wherein the cationic agent comprises a cationic lipid.

15. The nanoparticle of claim 9, wherein the cationic agent comprises a quaternary ammonium lipid.

16. The nanoparticle of claim 9, wherein the cationic agent comprises DOTAP.

17. The nanoparticle of claim 9, wherein the cationic agent comprises an aromatic amine.

18. The nanoparticle of claim 9, wherein the cationic agent comprises methotrexate.

19. The nanoparticle of claim 9, further comprising a corticosteroid.

20. The nanoparticle of claim 19, wherein the corticosteroid comprises a glucocorticoid.

21. The nanoparticle of claim 19, wherein the corticosteroid comprises betamethasone.

22. The nanoparticle of claim 9, wherein the ratio of the cationic agent to the therapeutic agent in weight percent is at least 1.0:1.

* * * * *